(12) United States Patent
Mattanovich et al.

(10) Patent No.: US 9,150,870 B2
(45) Date of Patent: Oct. 6, 2015

(54) CONSTITUTIVE PROMOTER

(71) Applicant: Lonza Ltd, Visp (CH)

(72) Inventors: Diethard Mattanovich, Vienna (AT); Brigitte Gasser, Vienna (AT); Roland Prielhofer, Vienna (AT)

(73) Assignee: Lonza Ltd., Visp (CH)

( * ) Notice: Subject to any disclaimer, the term of this patent is extended or adjusted under 35 U.S.C. 154(b) by 9 days.

(21) Appl. No.: 13/835,589

(22) Filed: Mar. 15, 2013

(65) Prior Publication Data
US 2014/0274761 A1 Sep. 18, 2014

(51) Int. Cl.
C12N 15/81 (2006.01)

(52) U.S. Cl.
CPC .............. C12N 15/815 (2013.01); C12N 15/81 (2013.01)

(58) Field of Classification Search
CPC ...................................................... C12N 15/815
USPC .............................................................. 506/9
See application file for complete search history.

(56) References Cited

U.S. PATENT DOCUMENTS

| 4,808,537 A | 2/1989 | Stroman et al. |
| 4,855,231 A | 8/1989 | Stroman et al. |
| 6,730,499 B1 | 5/2004 | Cregg |
| 2008/0153126 A1 | 6/2008 | Hartner et al. |
| 2011/0021378 A1 | 1/2011 | Callewaert et al. |

FOREIGN PATENT DOCUMENTS

| CN | 102180954 A | 9/2011 |
| EP | 0103409 A2 | 3/1984 |
| EP | 1951877 B1 | 11/2010 |
| WO | 9744470 A1 | 11/1997 |
| WO | 2005003310 A2 | 1/2005 |
| WO | 2007015178 A2 | 2/2007 |
| WO | WO2014066374 | * 5/2014 |

OTHER PUBLICATIONS

De Schutter et al., Jun. 2009, 27(6), pp. 561-566.*
DeSchutter et al., Genome sequence of the recombinant protein production host Pichia pastoris, Nature Biotechnol., 27(6):561-566 (2009).

(Continued)

Primary Examiner — Larry Riggs
Assistant Examiner — Karla Dines
(74) Attorney, Agent, or Firm — Meunier Carlin & Curfman LLC

(57) ABSTRACT

The invention relates to an isolated nucleic acid sequence comprising a promoter, which is a native sequence of Pichia pastoris comprising the nucleic acid sequence of pCS1 of SEQ ID NO:1, or a functionally active variant thereof which is a size variant, a mutant or hybrid of SEQ ID NO:1, or a combination thereof, expression constructs and recombinant host cells comprising the promoter, and a method of producing a protein of interest under the control of the promoter. It further relates to a method to identify a constitutive promoter from eukaryotic cells, and an isolated nucleic acid sequence comprising a promoter which when operatively linked to a nucleotide sequence encoding a protein of interest directs the expression thereof in a host cell at an expression level that is higher than under control of the native pGAP promoter at high and low growth rates.

20 Claims, 4 Drawing Sheets

(56) References Cited

OTHER PUBLICATIONS

Gasser et al., Engineering of biotin-prototrophy in *Pichia pastoris* for robust production processes, Metabolic Engineering, 12(6):573-580 (2010).

Marx et al., Directed gene copy number amplication in *Pichia pastoris* by vector integration into the ribosomal DNA locus, FEMS Yeast Res., 9:1260-1270 (2009).

Mattanovich et al., Genome, secretome and glucose transport highlight unique features of the protein production host *Pichia pastoris*, Microbial Cell Factories, 8:29 (2009).

Partial European Search Report for Application No. 13159527.4 dated May 31, 2013.

Qin et al., GAP Promoter Library for Fine-Tuning of Gene Expression in *Pichia pastoris*, Applied and Environmental Microbiology, 77:3600-3608 (2011).

Qin et al., Reliable high-throughput approach for screening of engineered constitutive promoters in the yeast *Pichia pastoris*, Letters in Applied Microbiology, 52(6):634-641 (2011).

Stadlmayr et al., Identification and characterisation of novel *Pichia pastoris* promoters for heterologous protein production, J. Biotechnol., 150(4):519-529 (2010).

Vassileva et al., Expression of hepatitis B surface antigen in the methylotrophic yeast *Pichia pastoris* using the GAP promoter. J. Biotechnol., 88(1):21-35 (2001).

\* cited by examiner

Fig. 1

SEQ ID NO:1

AGGGCATCATTGAGGTTTCCACAAAAGGAAGAAACATGGATCCAGAGACATCAACAGAGAGGAAAGCGGGT
AGTGAAGCCGAAGCCACAACACAGCCCGATTTGGAAGGGAGTTCACAATCAAGGTGAGTCCAGCCATTTTT
TTTCTTTTTTTTTTTTTATTCAGGTGAACCCACCTAACTATTTTAACTGGGATCCAGTGAGCTCGCTGG
GTGAAAGCCAACCATCTTTTGTTTCGGGGAACCGTGCTCGCCCCGTAAAGTTAATTTTTTTTCCCGCGCA
GCTTTAATCTTTCGGCAGAGAAGGCGTTTTCATCGTAGCGTGGGAACAGAATAATCAGTTCATGTGCTATA
CAGGCACATGGCAGCAGTCACTATTTTGCTTTTTAACCTTAAAGTCGTTCATCAATCATTAACTGACCAAT
CAGATTTTTTGCATTTGCCACTTATCTAAAAATACTTTTGTATCTCGCAGATACGTTCAGTGGTTTCCAGG
ACAACACCCAAAAAAAGGTATCAATGCCACTAGGCAGTCGGTTTTATTTTGGTCACCCACGCAAAGAAGC
ACCCACCTCTTTTAGGTTTTAAGTTGTGGGAACAGTAACACCGCCTAGAGCTTCAGGAAAAACCAGTACCT
GTGACCGCAATTCACCATGATGCAGAATGTTAATTTAAACGAGTGCCAAATCAAGATTTCAACAGACAAAT
CAATCGATCCATAGTTACCCATTCCAGCCTTTTCGTCGTCGAGCCTGCTTCATTCCTGCCTCAGGTGCATA
ACTTTGCATGAAAAGTCCAGATTAGGGCAGATTTTGAGTTTAAAATAGGAAATATAAACAAATATACCGCG
AAAAAGGTTTGTTTATAGCTTTTCGCCTGGTGCCGTACGGTATAAATACATACTCTCCTCCCCCCCTGGT
TCTCTTTTCTTTTGTTACTTACATTTTACCGTTCCGTCACTCGCTTCACTCAACAACAAAA

SEQ ID NO:2

GATAGTTCTAGAAGACCTGGCGTCGCTGGTCAACTACTCGTTTCACAAGTTGACAAAGACTTTTACCAAGA
GAAGAGCAGTTGTCACCGACCACAATAACAACCTGGAAGCCGAGAAAAAACTTGGAATCTCCAAGGTGAGA
CTGCCTAGAAATCCGTACTCTGCGGCCGATCGAAGACTGCATTTCCTCCAAGAATTGATGCTCATGGTCTC
ATCTTACAATCGCACACACAACAGTGTCAGTCTTCTTTGCGGTCCCTTGAACACAACCAACCGAAAGGTGG
GGAAGTCTAATGTCACGCAAACGATATTGCAACCAATGTTGGGCTCTACTGGCGTCTGGCTGCATCAAATA
GCTGATCGGTTCGTAATCTTCAAAGATTGGTGTAGGACGAACGAGTCTGCTGGGCTACAAGTTTTGCCCCA
TATCGCTGTTCAAGCCAACCCGCGGAATCCCAAAACACCCCATCCGACAAAAGTTGTTGTTTTCAGCAGAT
CTAGGGAGGGCATCATTGAGGTTTCCACAAAAGGAAGAAACATGGATCCAGAGACATCAACAGAGAGGAAA
GCGGGTAGTGAAGCCGAAGCCACAACACAGCCCGATTTGGAAGGGAGTTCACAATCAAGGTGAGTCCAGCC
ATTTTTTTTCTTTTTTTTTTTTTATTCAGGTGAACCCACCTAACTATTTTAACTGGGATCCAGTGAGCT
CGCTGGGTGAAAGCCAACCATCTTTTGTTTCGGGGAACCGTGCTCGCCCCGTAAAGTTAATTTTTTTTCC
CGCGCAGCTTTAATCTTTCGGCAGAGAAGGCGTTTTCATCGTAGCGTGGGAACAGAATAATCAGTTCATGT
GCTATACAGGCACATGGCAGCAGTCACTATTTTGCTTTTTAACCTTAAAGTCGTTCATCAATCATTAACTG
ACCAATCAGATTTTTGCATTTGCCACTTATCTAAAAATACTTTTGTATCTCGCAGATACGTTCAGTGGTT
TCCAGGACAACACCCAAAAAAAGGTATCAATGCCACTAGGCAGTCGGTTTTATTTTGGTCACCCACGCAA
AGAAGCACCCACCTCTTTTAGGTTTTAAGTTGTGGGAACAGTAACACCGCCTAGAGCTTCAGGAAAAACCA
GTACCTGTGACCGCAATTCACCATGATGCAGAATGTTAATTTAAACGAGTGCCAAATCAAGATTTCAACAG
ACAAATCAATCGATCCATAGTTACCCATTCCAGCCTTTTCGTCGTCGAGCCTGCTTCATTCCTGCCTCAGG
TGCATAACTTTGCATGAAAAGTCCAGATTAGGGCAGATTTTGAGTTTAAAATAGGAAATATAAACAAATAT
ACCGCGAAAAAGGTTTGTTTATAGCTTTTCGCCTGGTGCCGTACGGTATAAATACATACTCTCCTCCCCCC
CCTGGTTCTCTTTTCTTTTGTTACTTACATTTTACCGTTCCGTCACTCGCTTCACTCAACAACAAAA

SEQ ID NO:3

AGCCAACCATCTTTTGTTTCGGGGAACCGTGCTCGCCCCGTAAAGTTAATTTTTTTTCCCGCGCAGCTTT
AATCTTTCGGCAGAGAAGGCGTTTTCATCGTAGCGTGGGAACAGAATAATCAGTTCATGTGCTATACAGGC
ACATGGCAGCAGTCACTATTTTGCTTTTTAACCTTAAAGTCGTTCATCAATCATTAACTGACCAATCAGAT
TTTTGCATTTGCCACTTATCTAAAAATACTTTTGTATCTCGCAGATACGTTCAGTGGTTTCCAGGACAAC
ACCCAAAAAAGGTATCAATGCCACTAGGCAGTCGGTTTTATTTTGGTCACCCACGCAAAGAAGCACCCA
CCTCTTTTAGGTTTTAAGTTGTGGGAACAGTAACACCGCCTAGAGCTTCAGGAAAAACCAGTACCTGTGAC
CGCAATTCACCATGATGCAGAATGTTAATTTAAACGAGTGCCAAATCAAGATTTCAACAGACAAATCAATC

Fig. 1 (cont)

GATCCATAGTTACCCATTCCAGCCTTTTCGTCGTCGAGCCTGCTTCATTCCTGCCTCAGGTGCATAACTTT
GCATGAAAAGTCCAGATTAGGGCAGATTTTGAGTTTAAAATAGGAAATATAAACAAATATACCGCGAAAAA
GGTTTGTTTATAGCTTTTCGCCTGGTGCCGTACGGTATAAATACATACTCTCCTCCCCCCCCTGGTTCTCT
TTTTCTTTTGTTACTTACATTTTACCGTTCCGTCACTCGCTTCACTCAACAACAAAA

SEQ ID NO:4

GTGGTTTCCAGGACAACACCCAAAAAAGGTATCAATGCCACTAGGCAGTCGGTTTTATTTTTGGTCACCC
ACGCAAAGAAGCACCCACCTCTTTTAGGTTTTAAGTTGTGGGAACAGTAACACCGCCTAGAGCTTCAGGAA
AAACCAGTACCTGTGACCGCAATTCACCATGATGCAGAATGTTAATTTAAACGAGTGCCAAATCAAGATTT
CAACAGACAAATCAATCGATCCATAGTTACCCATTCCAGCCTTTTCGTCGTCGAGCCTGCTTCATTCCTGC
CTCAGGTGCATAACTTTGCATGAAAAGTCCAGATTAGGGCAGATTTTGAGTTTAAAATAGGAAATATAAAC
AAATATACCGCGAAAAAGGTTTGTTTATAGCTTTTCGCCTGGTGCCGTACGGTATAAATACATACTCTCCT
CCCCCCCCTGGTTCTCTTTTTCTTTGTTACTTACATTTTACCGTTCCGTCACTCGCTTCACTCAACAACA
AAA

SEQ ID NO:5

GACCGCAATTCACCATGATGCAGAATGTTAATTTAAACGAGTGCCAAATCAAGATTTCAACAGACAAATCA
ATCGATCCATAGTTACCCATTCCAGCCTTTTCGTCGTCGAGCCTGCTTCATTCCTGCCTCAGGTGCATAAC
TTTGCATGAAAAGTCCAGATTAGGGCAGATTTTGAGTTTAAAATAGGAAATATAAACAAATATACCGCGAA
AAAGGTTTGTTTATAGCTTTTCGCCTGGTGCCGTACGGTATAAATACATACTCTCCTCCCCCCCCTGGTTC
TCTTTTTCTTTGTTACTTACATTTTACCGTTCCGTCACTCGCTTCACTCAACAACAAAA

SEQ ID NO:6

AGCCTGCTTCATTCCTGCCTCAGGTGCATAACTTTGCATGAAAAGTCCAGATTAGGGCAGATTTTGAGTTT
AAAATAGGAAATATAAACAAATATACCGCGAAAAAGGTTTGTTTATAGCTTTTCGCCTGGTGCCGTACGGT
ATAAATACATACTCTCCTCCCCCCCCTGGTTCTCTTTTTCTTTTGTTACTTACATTTTACCGTTCCGTCAC
TCGCTTCACTCAACAACAAAA

SEQ ID NO:7

CCGCGAAAAAGGTTTGTTTATAGCTTTTCGCCTGGTGCCGTACGGTATAAATACATACTCTCCTCCCCCCC
CTGGTTCTCTTTTTCTTTTGTTACTTACATTTTACCGTTCCGTCACTCGCTTCACTCAACAACAAAA

SEQ ID NO:8

CATACTCTCCTCCCCCCCCTGGTTCTCTTTTTCTTTTGTTACTTACATTTTACCGTTCCGTCACTCGCTTC
ACTCAACAACAAAA

Fig. 2

SEQ ID NO:9

ATGCAATTCTCTATCGTCGCTACTTTGGCTCTTGCTGGTTCCGCTCTGGCTGCTTACTCTAACGTAACTTA
CACTTACGAGACTACCATCACCGATGTTGTCACCGAGCTCACCACTTACTGCCCAGAGCCAACCACCTTCG
TTCACAAGAACAAGACCATCACTGTGACCGCCCCAACCACTTTGACCATCACTGACTGTCCTTGCACCATC
TCCAAGACCACCAAGATCACCACTGATGTTCCACCAACCACCCACTCCACCCCACACACCACCACCACTCA
CGTGCCATCTACCTCTACCCCAGCTCCAACCCACTCTGTTTCTACCATCTCTCACGGTGGTGCTGCTAAGG
CTGGTGTTGCTGGTTTGGCCGGTGTTGCTGCTGCCGCTGCTTACTTCTTGTAA

SEQ ID NO:10

MQFSIVATLALAGSALAAYSNVTYTYETTITDVVTELTTYCPEPTTFVHKNKTITVTAPTTLTITDCPCTI
SKTTKITTDVPPTTHSTPHTTTTHVPSTSTPAPTHSVSTISHGGAAKAGVAGLAGVAAAAAYFL

SEQ ID NO:11

ATGCAATTCTCTATCGTCGCTACTTTGGCTCTTGCTGGTTCCGCTCTGGCTGCTTACTC
TAACGTAACTTACACTTACGAGACTACCATCACCGATGTTGTCACTGAGTTGACCACTT
ACTGCCCAGAGCCAACCACCTTTGTTTACAAGAACAAGACCATCACCGTGACTGAGCCA
ACCACTTTGACCATCACTGACTGCCCATGCACCATCTCAAAGACCACCAAGATCACCAC
TGATGTTCCACCAACCACCCACGTCACCCCATCCACCACTCACGTGCCATCTACCTCTA
CCCCAGCTCCAACCCACTCTGTTTCTACCATCTCTCACGGTGGTGCTGCTAAGGCTGGT
GTTGCTGGTTTGGCCGGTGTTGCTGCTGCCGCTGCTTACTTCTTGTAA

SEQ ID NO:12

MQFSIVATLALAGSALAAYSNVTYTYETTITDVVTELTTYCPEPTTFVYKNKTITVTEPTTLTITDCPCTI
SKTTKITTDVPPTTHVTPSTTHVPSTSTPAPTHSVSTISHGGAAKAGVAGLAGVAAAAAYFL

Fig. 3

SEQ ID NO:13

CTTTTTTGTAGAAATGTCTTGGTGTCCTCGTCCAATCAGGTAGCCATCTCTGAAATATC
TGGCTCCGTTGCAACTCCGAACGACCTGCTGGCAACGTAAAATTCTCCGGGGTAAAACT
TAAATGTGGAGTAATGGAACCAGAAACGTCTCTTCCCTTCTCTCTCCTTCCACCGCCCG
TTACCGTCCCTAGGAAATTTTACTCTGCTGGAGAGCTTCTTCTACGGCCCCCTTGCAGC
AATGCTCTTCCCAGCATTACGTTGCGGGTAAAACGGAGGTCGTGTACCCGACCTAGCAG
CCCAGGGATGGAAAAGTCCCGGCCGTCGCTGGCAATAATAGCGGGCGGACGCATGTCAT
GAGATTATTGGAAACCACCAGAATCGAATATAAAAGGCGAACACCTTTCCCAATTTTGG
TTTCTCCTGACCCAAAGACTTTAAATTTAATTTATTTGTCCCTATTTCAATCAATTGAA
CAACTATCACCTGCAGGCC

SEQUENCE LISTING

<160> NUMBER OF SEQ ID NOS: 23

<210> SEQ ID NO 1
<211> LENGTH: 985
<212> TYPE: DNA
<213> ORGANISM: Pichia pastoris

<400> SEQUENCE: 1

```
agggcatcat tgaggtttcc acaaaaggaa gaaacatgga tccagagaca tcaacagaga      60
ggaaagcggg tagtgaagcc gaagccacaa cacagcccga tttggaaggg agttcacaat     120
caaggtgagt ccagccattt tttttctttt ttttttttt attcaggtga acccacctaa     180
ctatttttaa ctgggatcca gtgagctcgc tgggtgaaag ccaaccatct tttgtttcgg     240
ggaaccgtgc tcgccccgta aagttaattt ttttttcccg cgcagcttta atctttcggc     300
agagaaggcg ttttcatcgt agcgtgggaa cagaataatc agttcatgtg ctatacaggc     360
acatggcagc agtcactatt ttgctttta accttaaagt cgttcatcaa tcattaactg     420
accaatcaga ttttttgcat ttgccactta tctaaaaata cttttgtatc tcgcagatac     480
gttcagtggt ttccaggaca acacccaaaa aaaggtatca atgccactag gcagtcggtt     540
ttatttttgg tcacccacgc aaagaagcac ccacctcttt taggttttaa gttgtgggaa     600
cagtaacacc gcctagagct tcaggaaaaa ccagtacctg tgaccgcaat tcaccatgat     660
gcagaatgtt aatttaaacg agtgccaaat caagatttca acagacaaat caatcgatcc     720
atagttaccc attccagcct tttcgtcgtc gagcctgctt cattcctgcc tcaggtgcat     780
aactttgcat gaaaagtcca gattagggca gattttgagt ttaaaatagg aaatataaac     840
aaatataccg cgaaaaaggt ttgtttatag cttttcgcct ggtgccgtac ggtataaata     900
catactctcc tcccccccct ggttctcttt ttcttttgtt acttacattt taccgttccg     960
tcactcgctt cactcaacaa caaaa                                           985
```

<210> SEQ ID NO 2
<211> LENGTH: 1488
<212> TYPE: DNA
<213> ORGANISM: Pichia pastoris

<400> SEQUENCE: 2

```
gatagttcta gaagacctgg cgtcgctggt caactactcg tttcacaagt tgacaaagac      60
```

```
ttttaccaag agaagagcag ttgtcaccga ccacaataac aacctggaag ccgagaaaaa      120
acttggaatc tccaaggtga gactgcctag aaatccgtac tctgcggccg atcgaagact      180
gcatttcctc caagaattga tgctcatggt ctcatcttac aatcgcacac acaacagtgt      240
cagtcttctt tgcggtccct tgaacacaac caaccgaaag gtggggaagt ctaatgtcac      300
gcaaacgata ttgcaaccaa tgttgggctc tactggcgtc tggctgcatc aaatagctga      360
tcggttcgta atcttcaaag attggtgtag gacgaacgag tctgctgggc tacaagtttt      420
gccccatatc gctgttcaag ccaacccgcg gaatcccaaa acaccccatc cgacaaaagt      480
tgttgttttc agcagatcta gggagggcat cattgaggtt tccacaaaag gaagaaacat      540
ggatccagag acatcaacag agaggaaagc gggtagtgaa gccgaagcca acacagcc       600 cgatttggaa gggagttcac aatcaaggtg agtccagcca ttttttttct ttttttttt       660 tttattcagg tgaacccacc taactatttt taactgggat ccagtgagct cgctgggtga      720
aagccaacca tcttttgttt cggggaaccg tgctcgcccc gtaaagttaa ttttttttc       780 ccgcgcagct ttaatctttc ggcagagaag gcgttttcat cgtagcgtgg aacagaata       840 atcagttcat gtgctataca ggcacatggc agcagtcact attttgcttt ttaaccttaa      900
agtcgttcat caatcattaa ctgaccaatc agattttttg catttgccac ttatctaaaa      960
atacttttgt atctcgcaga tacgttcagt ggtttccagg acaacaccca aaaaaaggta     1020
tcaatgccac taggcagtcg gttttatttt tggtcaccca cgcaaagaag cacccacctc     1080
ttttaggttt taagttgtgg aacagtaaca accgcctaga gcttcaggaa aaaccagtac     1140
ctgtgaccgc aattcaccat gatgcagaat gttaatttaa acgagtgcca atcaagatt      1200 tcaacagaca aatcaatcga tccatagtta cccattccag cctttcgtc gtcgagcctg      1260 cttcattcct gcctcaggtg cataactttg catgaaaagt ccagattagg gcagattttg     1320
agtttaaaat aggaaatata acaaatata ccgcgaaaaa ggtttgttta tagcttttcg      1380
cctggtgccg tacggtataa atacatactc tcctccccc cctggttctc ttttctttt      1440 gttacttaca ttttaccgtt ccgtcactcg cttcactcaa caacaaaa                  1488
```

<210> SEQ ID NO 3
<211> LENGTH: 767
<212> TYPE: DNA
<213> ORGANISM: Pichia pastoris

<400> SEQUENCE: 3

```
agccaaccat cttttgtttc ggggaaccgt gctcgccccg taaagttaat ttttttttcc      60
cgcgcagctt taatctttcg gcagagaagg cgttttcatc gtagcgtggg aacagaataa     120
tcagttcatg tgctatacag gcacatggca gcagtcacta ttttgctttt taaccttaaa     180
gtcgttcatc aatcattaac tgaccaatca gattttttgc atttgccact tatctaaaaa     240 tactttttgta tctcgcagat acgttcagtg gtttccagga caacacccaa aaaaggtat     300 caatgccact aggcagtcgg ttttattttt ggtcacccac gcaaagaagc acccacctct     360
tttaggtttt aagttgtggg aacagtaaca ccgcctagag cttcaggaaa aaccagtacc     420
tgtgaccgca attcaccatg atgcagaatg ttaatttaaa cgagtgccaa atcaagattt     480
caacagacaa atcaatcgat ccatagttac ccattccagc cttttcgtcg tcgagcctgc     540
ttcattcctg cctcaggtgc ataactttgc atgaaaagtc cagattaggg cagattttga     600
gtttaaaata ggaaatataa acaaatatac cgcgaaaaag gtttgtttat agcttttcgc     660
```

```
ctggtgccgt acggtataaa tacatactct cctcccccc ctggttctct ttttcttttg      720
ttacttacat tttaccgttc cgtcactcgc ttcactcaac aacaaaa                   767

<210> SEQ ID NO 4
<211> LENGTH: 500
<212> TYPE: DNA
<213> ORGANISM: Pichia pastoris

<400> SEQUENCE: 4
gtggtttcca ggacaacacc caaaaaagg tatcaatgcc actaggcagt cggttttatt      60
tttggtcacc cacgcaaaga agcacccacc tcttttaggt tttaagttgt gggaacagta    120
acaccgccta gagcttcagg aaaaaccagt acctgtgacc gcaattcacc atgatgcaga    180
atgttaattt aaacgagtgc caaatcaaga tttcaacaga caatcaatc gatccatagt     240 tacccattcc agccttttcg tcgtcgagcc tgcttcattc ctgcctcagg tgcataactt    300
tgcatgaaaa gtccagatta gggcagattt tgagtttaaa ataggaaata taaacaaata    360
taccgcgaaa aaggtttgtt tatagctttt cgcctggtgc cgtacggtat aaatacatac    420
tctcctcccc ccctggttc tcttttctt tgttactta catttaccg ttccgtcact        480 cgcttcactc aacaacaaaa                                                500

<210> SEQ ID NO 5
<211> LENGTH: 344
<212> TYPE: DNA
<213> ORGANISM: Pichia pastoris

<400> SEQUENCE: 5
gaccgcaatt caccatgatg cagaatgtta atttaaacga gtgccaaatc aagatttcaa     60
cagacaaatc aatcgatcca tagttaccca ttccagcctt ttcgtcgtcg agcctgcttc    120
attcctgcct caggtgcata actttgcatg aaaagtccag attagggcag attttgagtt    180
taaaatagga aatataaaca aatataccgc gaaaaaggtt tgtttatagc ttttcgcctg    240
gtgccgtacg gtataaatac atactctcct ccccccctg ttctctttt tcttttgtta     300 cttacatttt accgttccgt cactcgcttc actcaacaac aaaa                     344

<210> SEQ ID NO 6
<211> LENGTH: 234
<212> TYPE: DNA
<213> ORGANISM: Pichia pastoris

<400> SEQUENCE: 6
agcctgcttc attcctgcct caggtgcata actttgcatg aaaagtccag attagggcag     60
attttgagtt taaaatagga aatataaaca aatataccgc gaaaaaggtt tgtttatagc    120
ttttcgcctg gtgccgtacg gtataaatac atactctcct ccccccctg ttctctttt     180 tcttttgtta cttacatttt accgttccgt cactcgcttc actcaacaac aaaa          234

<210> SEQ ID NO 7
<211> LENGTH: 138
<212> TYPE: DNA
<213> ORGANISM: Pichia pastoris

<400> SEQUENCE: 7
ccgcgaaaaa ggtttgttta tagcttttcg cctggtgccg tacggtataa atacatactc     60
tcctcccccc cctggttctc ttttctttt gttacttaca ttttaccgtt ccgtcactcg    120
cttcactcaa caacaaaa                                                  138
```

<210> SEQ ID NO 8
<211> LENGTH: 85
<212> TYPE: DNA
<213> ORGANISM: Pichia pastoris

<400> SEQUENCE: 8
catactctcc tcccccccct ggttctcttt ttcttttgtt acttacatttt taccgttccg    60 tcactcgctt cactcaacaa caaaa                                          85

<210> SEQ ID NO 9
<211> LENGTH: 408
<212> TYPE: DNA
<213> ORGANISM: Pichia pastoris

<400> SEQUENCE: 9
atgcaattct ctatcgtcgc tactttggct cttgctggtt ccgctctggc tgcttactct    60
aacgtaactt acacttacga gactaccatc accgatgttg tcaccgagct caccacttac   120
tgcccagagc caaccacctt cgttcacaag aacaagacca tcactgtgac cgccccaacc   180
actttgacca tcactgactg tccttgcacc atctccaaga ccaccaagat caccactgat   240
gttccaccaa ccacccactc caccccacac accaccacca ctcacgtgcc atctacctct   300
accccagctc caacccactc tgtttctacc atctctcacg gtggtgctgc taaggctggt   360
gttgctggtt tggccggtgt tgctgctgcc gctgcttact tcttgtaa              408

<210> SEQ ID NO 10
<211> LENGTH: 135
<212> TYPE: PRT
<213> ORGANISM: Pichia pastoris

<400> SEQUENCE: 10

Met Gln Phe Ser Ile Val Ala Thr Leu Ala Leu Ala Gly Ser Ala Leu
1               5                   10                  15

Ala Ala Tyr Ser Asn Val Thr Tyr Thr Tyr Glu Thr Thr Ile Thr Asp
            20                  25                  30

Val Val Thr Glu Leu Thr Thr Tyr Cys Pro Glu Pro Thr Thr Phe Val
        35                  40                  45

His Lys Asn Lys Thr Ile Thr Val Thr Ala Pro Thr Thr Leu Thr Ile
    50                  55                  60

Thr Asp Cys Pro Cys Thr Ile Ser Lys Thr Thr Lys Ile Thr Thr Asp
65                  70                  75                  80

Val Pro Pro Thr Thr His Ser Thr Pro His Thr Thr Thr His Val
                85                  90                  95

Pro Ser Thr Ser Thr Pro Ala Pro Thr His Ser Val Ser Thr Ile Ser
            100                 105                 110

His Gly Gly Ala Ala Lys Ala Gly Val Ala Gly Leu Ala Gly Val Ala
        115                 120                 125

Ala Ala Ala Ala Tyr Phe Leu
    130                 135

<210> SEQ ID NO 11
<211> LENGTH: 402
<212> TYPE: DNA
<213> ORGANISM: Pichia pastoris

<400> SEQUENCE: 11
atgcaattct ctatcgtcgc tactttggct cttgctggtt ccgctctggc tgcttactct    60

```
aacgtaactt acacttacga gactaccatc accgatgttg tcactgagtt gaccacttac      120
tgcccagagc caaccacctt tgtttacaag aacaagacca tcaccgtgac tgagccaacc      180
actttgacca tcactgactg cccatgcacc atctcaaaga ccaccaagat caccactgat      240
gttccaccaa ccaccacgt caccccatcc accactcacg tgccatctac ctctaccccca     300 gctccaaccc actctgtttc taccatctct cacggtggtg ctgctaaggc tggtgttgct      360
ggtttggccg gtgttgctgc tgccgctgct tacttcttgt aa                        402
```

```
<210> SEQ ID NO 12
<211> LENGTH: 133
<212> TYPE: PRT
<213> ORGANISM: Pichia pastoris

<400> SEQUENCE: 12

Met Gln Phe Ser Ile Val Ala Thr Leu Ala Leu Ala Gly Ser Ala Leu
1               5                   10                  15

Ala Ala Tyr Ser Asn Val Thr Tyr Thr Tyr Glu Thr Thr Ile Thr Asp
            20                  25                  30

Val Val Thr Glu Leu Thr Thr Tyr Cys Pro Glu Pro Thr Thr Phe Val
        35                  40                  45

Tyr Lys Asn Lys Thr Ile Thr Val Thr Glu Pro Thr Thr Leu Thr Ile
    50                  55                  60

Thr Asp Cys Pro Cys Thr Ile Ser Lys Thr Thr Lys Ile Thr Thr Asp
65                  70                  75                  80

Val Pro Pro Thr Thr His Val Thr Pro Ser Thr Thr His Val Pro Ser
                85                  90                  95

Thr Ser Thr Pro Ala Pro Thr His Ser Val Ser Thr Ile Ser His Gly
            100                 105                 110

Gly Ala Ala Lys Ala Gly Val Ala Gly Leu Ala Gly Val Ala Ala Ala
        115                 120                 125

Ala Ala Tyr Phe Leu
    130
```

```
<210> SEQ ID NO 13
<211> LENGTH: 491
<212> TYPE: DNA
<213> ORGANISM: Pichia pastoris

<400> SEQUENCE: 13
cttttttgta gaaatgtctt ggtgtcctcg tccaatcagg tagccatctc tgaaatatct       60
ggctccgttg caactccgaa cgacctgctg gcaacgtaaa attctccggg gtaaaactta      120
aatgtggagt aatggaacca gaaacgtctc ttcccttctc tctccttcca ccgcccgtta     180
ccgtccctag gaaattttac tctgctggag agcttcttct acggccccct gcagcaatg     240 ctcttcccag cattacgttg cgggtaaaac ggaggtcgtg tacccgacct agcagcccag     300
ggatggaaaa gtcccggccg tcgctggcaa taatagcggg cggacgcatg tcatgagatt     360
attggaaacc accagaatcg aatataaaag gcgaacacct ttcccaattt tggtttctcc     420
tgacccaaag actttaaatt taatttattt gtccctattt caatcaattg aacaactatc     480
acctgcaggc c                                                          491
```

```
<210> SEQ ID NO 14
<211> LENGTH: 33
<212> TYPE: DNA
<213> ORGANISM: artificial
```

```
<220> FEATURE:
<223> OTHER INFORMATION: Primer

<400> SEQUENCE: 14
gatagggccc cagggcatca ttgaggtttc cac                              33

<210> SEQ ID NO 15
<211> LENGTH: 36
<212> TYPE: DNA
<213> ORGANISM: artificial
<220> FEATURE:
<223> OTHER INFORMATION: Primer

<400> SEQUENCE: 15
gatacctgca ggttttgttg ttgagtgaag cgagtg                           36

<210> SEQ ID NO 16
<211> LENGTH: 33
<212> TYPE: DNA
<213> ORGANISM: artificial
<220> FEATURE:
<223> OTHER INFORMATION: Primer

<400> SEQUENCE: 16
gatagggccc cagggcatca ttgaggtttc cac                              33

<210> SEQ ID NO 17
<211> LENGTH: 35
<212> TYPE: DNA
<213> ORGANISM: artificial
<220> FEATURE:
<223> OTHER INFORMATION: Primer

<400> SEQUENCE: 17
gatagggccc gatagttcta aagacctgg cgtcg                             35

<210> SEQ ID NO 18
<211> LENGTH: 31
<212> TYPE: DNA
<213> ORGANISM: artificial
<220> FEATURE:
<223> OTHER INFORMATION: Primer

<400> SEQUENCE: 18
gatagggccc agccaaccat cttttgtttc g                                31

<210> SEQ ID NO 19
<211> LENGTH: 31
<212> TYPE: DNA
<213> ORGANISM: artificial
<220> FEATURE:
<223> OTHER INFORMATION: Primer

<400> SEQUENCE: 19
gatagggccc gtggtttcca ggacaacacc c                                31

<210> SEQ ID NO 20
<211> LENGTH: 31
<212> TYPE: DNA
<213> ORGANISM: artificial
<220> FEATURE:
<223> OTHER INFORMATION: Primer

<400> SEQUENCE: 20
gatagggccc gaccgcaatt caccatgatg c                                31
```

```
<210> SEQ ID NO 21
<211> LENGTH: 29
<212> TYPE: DNA
<213> ORGANISM: artificial
<220> FEATURE:
<223> OTHER INFORMATION: Primer

<400> SEQUENCE: 21
gatagggccc agcctgcttc attcctgcc                                29

<210> SEQ ID NO 22
<211> LENGTH: 33
<212> TYPE: DNA
<213> ORGANISM: artificial
<220> FEATURE:
<223> OTHER INFORMATION: Primer

<400> SEQUENCE: 22
gatagggccc ccgcgaaaaa ggtttgttta tag                           33

<210> SEQ ID NO 23
<211> LENGTH: 31
<212> TYPE: DNA
<213> ORGANISM: artificial
<220> FEATURE:
<223> OTHER INFORMATION: Primer

<400> SEQUENCE: 23
gatagggccc catactctcc tcccccccct g                             31
```

CONSTITUTIVE PROMOTER

The invention refers to an isolated nucleic acid sequence comprising a strong constitutive promoter and a method of producing a protein of interest in a eukaryotic cell culture under the control of such a promoter.

BACKGROUND

Successful production of recombinant proteins has been accomplished with eukaryotic hosts. The most prominent examples are yeasts like *Saccharomyces cerevisiae*, *Pichia pastoris* or *Hansenula polymorpha*, filamentous fungi like *Aspergillus awamori* or *Trichoderma reesei*, or mammalian cells like e.g. CHO cells. While the production of some proteins is readily achieved at high rates, many other proteins are only obtained at comparatively low levels.

The heterologous expression of a gene in a host organism usually requires a vector allowing stable transformation of the host organism. A vector would provide the gene with a functional promoter adjacent to the 5' end of the coding sequence. The transcription is thereby regulated and initiated by this promoter sequence. Most promoters used up to date have been derived from genes that code for proteins that are usually present at high concentrations in the cell.

EP0103409A2 discloses the use of yeast promoters associated with expression of specific enzymes in the glycolytic pathway, i.e. promoters involved in expression of pyruvate kinase, triosephosphate isomerase, phosphoglucose isomerase, phosphor-glycerate mutase, hexokinase 1 and 2, glucokinase, phosphofructose kinase, aldolase and glycolytic regulation gene.

WO 97/44470 describes yeast promoters from *Yarrowia lipolytica* for the translation elongation factor 1 (TEF1) protein and for the ribosomal protein S7 that are suitable for heterologous expression of proteins in yeast, and EP1951877A1 describes the use of the *P. pastoris* TEF1 promoter for the production of heterologous proteins.

WO2005003310 provides methods for the expression of a coding sequence of interest in yeast using a promoter of the glyceraldehyde-3-phosphate dehydrogenase or phosphoglycerate mutase from oleaginous yeast *Yarrowia lipolytica*.

Promoter sequences derived from genes involved in the methanol metabolic pathway of *Pichia pastoris* are disclosed in U.S. Pat. No. 4,808,537 and U.S. Pat. No. 4,855,231 (alcohol oxidase AOX1, AOX2) and U.S. Pat. No. 6,730,499B1 (formaldehyde dehydrogenase FLD1). US20080153126A1 includes mutant promoter sequences based on the AOX1 promoter.

The AOX1 promoter is induced only in response to methanol and repressed by other carbon sources, such as glucose or ethanol. Methanol has the disadvantage that it is unsuitable for use in the production of certain products, since it is potentially hazardous for its toxicity and flammability. Therefore, alternatives to the AOX1 promoter are sought.

Vassileva et al. (J. Biotechnol. (2001) 88: 21-35) describe the use of the GAP promoter to express HBsAg in *P. pastoris*, using multicopy expression cassettes as an alternative to the AOX1 promoter. The constitutive system was proposed for continuous culture to permit maintenance of the cells in mid-exponential phase.

Promoters used in *Pichia pastoris* are either tightly regulated (like pAOX or pFLD) being active on specific substrates such as methanol, or they are constitutively active in many different conditions, media and substrates. Among the constitutive ones, especially the GAP and the TEF promoters have been described to be strong, and useful for recombinant protein production.

However, it was shown that the activity of both constitutive promoters is not constantly strong during a fed-batch production process. Especially in the later phases of the process, when cell growth rates are slow, also the activity of the promoters in getting low, thus limiting expression levels of the gene of interest (GOI) and production yields (Stadlmayr et al. 2010. J Biotechnol. 150: 519-529).

Selection of suitable promoters is not intuitive or rational, as even highly abundant glycolytic enzymes such as enolase (ENO), triose phosphate isomerase (TPI) or glucose-6-phosphate isomerase (PGI) do not have promoters that are as strong as pGAP and pTEF (Stadlmayr et al. 2010. J Biotechnol. 150: 519-529; Gasser et al. 2010. Metabolic Engineering 12:573-580).

Qin et al. (Applied and Environmental Microbiology (2011) 3600-3608) describe a GAP promoter library and various mutants with varying activities.

It is desirable to provide improved recombinant eukaryotic cell lines to produce fermentation products that can be isolated with high yields. Therefore, it is the object of the present invention to provide for alternative regulatory elements suitable for recombinant production methods, which are simple and efficient.

SUMMARY OF THE INVENTION

The object is solved by the subject matter as claimed.

According to the invention there is provided an isolated nucleic acid sequence comprising a promoter, which is a native sequence of *Pichia pastoris* comprising the nucleic acid sequence of pCS1 of SEQ ID NO:1, or a functionally active variant thereof which is a size variant, a mutant or hybrid of SEQ ID NO:1, or a combination thereof.

Specifically, the functionally active variant is a) a size variant of pCS1 of SEQ ID NO:1, preferably comprising the nucleic acid sequence selected from the group consisting of SEQ ID NOs:2, 3, 4, 5, 6, 7 and 8;

b) a mutant of the pCS1 of SEQ ID NO:1, or a mutant of the size variant of a), which mutant has at least 60% homology to the sequence SEQ ID NO:1 or to the size variant;

c) a hybrid comprising
  a sequence selected from the group consisting of pCS1 of SEQ ID NO:1, a size variant of a), and a mutant of b); and
  at least one further sequence selected from the group consisting of pCS1 of SEQ ID NO:1, a size variant of a), a mutant of b), and a heterologous sequence; or d) a sequence which hybridizes under stringent conditions to any of the size variant, or the mutant nucleic acid sequences of a), or b).

According to a specific embodiment, the functionally active variant is selected from the group consisting of homologs with
  i) at least about 60% nucleotide sequence identity;
  ii) homologs obtainable by modifying the nucleotide sequence of pCS1 of SEQ ID NO:1 or size variants thereof, by insertion, deletion or substitution of one or more nucleotides within the sequence or at either or both of the distal ends of the sequence, preferably with a nucleotide sequence of 80 bp to 1500 bp, more preferably at least 200 bp; and
  iii) analogs derived from species other than *Pichia pastoris*.

Specifically the functionally active variant of the invention has substantially the same promoter activity as pCS1.

According to a specific embodiment, the nucleic acid sequence is operably linked to a nucleotide sequence encoding a protein of interest (POI), which nucleic acid is not natively associated with the nucleotide sequence encoding the POI.

The invention further provides for an expression construct comprising a nucleic acid sequence of the invention, preferably an autonomously replicating vector or plasmid, or one which integrates into the chromosomal DNA of a host cell.

The invention further provides for a recombinant host cell which comprises the nucleic acid sequence of the invention or the expression construct of the invention, preferably a eukaryotic cell, more preferably a yeast or filamentous fungal cell, more preferably a yeast cell of the *Saccharomyces* or *Pichia* genus.

The invention further provides for a stable culture of a plurality of the cell of the invention.

The invention further provides for a method of producing a POI by culturing a recombinant host cell line comprising the nucleic acid sequence or the promoter of the invention, or the expression construct of the invention, and a nucleic acid encoding the POI under the transcriptional control of said promoter, comprising the steps of a) cultivating the cell line under conditions to express said POI, and b) recovering the POI.

Specifically, the POI is expressed under growth-limiting conditions, e.g. by cultivating the cell line at a growth rate of less than the maximal growth rate, typically less than 90%, preferably less than 80%, less than 70%, less than 60%, less than 50%, less than 40%, less than 30%, less than 20%, less than 10%, less than 5%, less than 3%, less than 2%, less than 1%, less than 0.5%, less than 0.4%, less than 0.3%, or less than 0.2% of the maximum growth rate of the cells. Typically the maximum growth rate is individually determined for a specific host cell.

According to a specific embodiment, the cell line is cultivated under batch, fed-batch or continuous cultivation conditions, and/or in media containing limited carbon substrate.

Specifically, the host cells are grown in a carbon source rich medium during the phase of high growth rate (e.g. at least 50%, or at least 60%, at least 70%, at least 80%, at least 90%, at least 95%, at least 98%, at least 99%, or up to the maximum growth rate) and producing the POI during a phase of low growth rate (e.g. less than 90%, preferably less than 80%, less than 70%, less than 60%, less than 50%, or less than 40%, less than 30%, less than 20%, less than 10%, less than 5%, less than 3%, less than 2%, less than 1%, less than 0.5%, less than 0.4%, less than 0.3%, or less than 0.2% of the maximum growth rate) e.g. while limiting the carbon source, preferably by feeding a defined minimal medium. Specifically the defined minimal medium does not comprise a transcription-inducing carbon source.

The POI is specifically a heterologous protein, preferably selected from therapeutic proteins, including antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI, specifically including a cell metabolite of the recombinant cell culture that expresses a gene of interest under the transcriptional control of a promoter of the invention.

The invention further provides for a method to identify a constitutive promoter from eukaryotic cells, comprising the steps of a) cultivating eukaryotic cells at a high growth rate;

b) further cultivating the cells at a low growth rate;

c) providing samples of the cell culture of step a) and b), d) performing transcription analysis in said samples and comparing the transcript levels with the transcript levels of the native pGAP promoter of the cells; and f) selecting the constitutive promoter that has a higher transcription strength as compared to the native pGAP promoter at high and low growth rates, preferably by determining a transcript level of the identified constitutive promoter which is at least 1.1-fold higher as compared to the native pGAP promoter, preferably at least 1.2-fold, preferably at least 1.3-fold, preferably at least 1.4-fold, preferably at least 1.5-fold, preferably at least 1.6-fold, preferably at least 1.7-fold, preferably at least 1.8-fold, preferably at least 1.9-fold, preferably at least 2-fold, preferably at least 3-fold, preferably at least 4-fold, preferably at least 5-fold, preferably at least 10-fold, or at least 15-fold higher.

Specifically, the transcript level is determined at a high growth rate and a low growth rate within the range of 0.01 to 0.2 $h^{-1}$, preferably within the range of 0.015 to 0.15 $h^{-1}$, e.g. by examining at least two samples of a cell culture, a first one representing a high growth rate, such as at least 0.05 $h^{-1}$, preferably at least 0.06 $h^{-1}$, or at least 0.07 $h^{-1}$, at least 0.08 $h^{-1}$, at least 0.09 $h^{-1}$, at least 0.1 $h^{-1}$, e.g. at a growth rate of 0.15 $h^{-1}$, and a second one representing a low growth rate, such as less than the first one, e.g. less than 0.05 $h^{-1}$, preferably less than 0.04 $h^{-1}$, less than 0.03 $h^{-1}$, or less than 0.02 $h^{-1}$, e.g. at a growth rate of 0.015 $h^{-1}$. The transcription level is specifically determined by analysis of the gene expression patterns using DNA microarrays, e.g. according to Example 11 below.

The invention further provides for an isolated nucleic acid sequence comprising a promoter which when operatively linked to a nucleotide sequence encoding a POI directs the expression thereof in a host cell at an expression level that is higher than under control of the native pGAP promoter at high and low growth rates.

Specifically, the expression level is determined at a high growth rate and a low growth rate within the range of 0.01 to 0.2 $h^{-1}$, preferably within the range of 0.015 to 0.15 $h^{-1}$, e.g. by examining at least two samples of a cell culture, a first one representing a high growth rate, such as at least 0.05 $h^{-1}$, preferably at least 0.06 $h^{-1}$, or at least 0.07 $h^{-1}$, at least 0.08 $h^{-1}$, at least 0.09 $h^{-1}$, at least 0.1 $h^{-1}$, e.g. at a growth rate of 0.15 $h^{-1}$, and a second one representing a low growth rate, such as less than the first one, e.g. less than 0.05 $h^{-1}$, preferably less than 0.04 $h^{-1}$, less than 0.03 $h^{-1}$, or less than 0.02 $h^{-1}$, e.g. at a growth rate of 0.015 $h^{-1}$. The expression level is specifically determined under growth-limited conditions. An example of determining the expression strength in growth-limited conditions e.g. in a glucose-limited chemostat cultivation, at high and low growth rates is provided in Example 10 below.

Specifically, the expression level is at least 1.1-fold higher compared to the pGAP promoter, preferably at least 1.2-fold, preferably at least 1.3-fold, preferably at least 1.4-fold, preferably at least 1.5-fold, preferably at least 1.6-fold, preferably at least 1.7-fold, preferably at least 1.8-fold, preferably at least 1.9-fold, preferably at least 2-fold, preferably at least 3-fold, preferably at least 4-fold, preferably at least 5-fold, preferably at least 10-fold, or at least 15-fold higher.

FIGURES

FIG. 1: Nucleic acid sequence pCS1 (985 bp, SEQ ID NO:1) of *P. pastoris*, and promoter sequences which are DNA sequences including pCS1 and additional nucleotides at the 5' end, or pCS1 fragments, promoting expression of CS1 in *P. pastoris*, which comprise 1488 bp (SEQ ID NO:2), 767 bp (SEQ ID NO:3), 500 bp (SEQ ID NO:4), 344 bp (SEQ ID NO:5), 234 bp (SEQ ID NO:6), 138 bp (SEQ ID NO:7) and 85 bp (SEQ ID NO:8).

FIG. 2: Sequences of CS1 coding nucleotide sequence and amino acid sequence i) of strains GS115, CBS7435 and CBS2612 (PAS_chr1-4_0586), coding sequence (SEQ ID NO:9), translated sequence (XM_002490678.1, SEQ ID NO:10); and ii) of strain DSMZ70382 (PIPA02805), coding sequence (SEQ ID NO:11), translated sequence (SEQ ID NO:12).

FIG. 3: Native pGAP promoter sequence of *P. pastoris* (GS115) (SEQ ID NO:13).

DETAILED DESCRIPTION OF THE INVENTION

Specific terms as used throughout the specification have the following meaning.

The term "carbon source" or "carbon substrate" as used herein shall mean a fermentable carbon substrate, typically a source carbohydrate, suitable as an energy source for microorganisms, such as those capable of being metabolized by host organisms or production cell lines, in particular sources selected from the group consisting of monosaccharides, oligosaccharides, polysaccharides, alcohols including glycerol, in the purified form, in minimal media or provided in raw materials, such as a complex nutrient material. The carbon source may be used according to the invention as a single carbon source or as a mixture of different carbon sources.

The term "carbon substrate rich conditions" as used herein specifically refers to the type and amount of a carbon substrate suitable for cell growth, such as a nutrient for eukaryotic cells. The carbon source may be provided in a medium, such as a basal medium or complex medium, but also in a (chemically) defined medium containing a purified carbon source. The carbon source for use in a growth phase of a cell cultivation process is herein also called "basal carbon source" and typically provided in an amount to provide for cell growth, for example to obtain cell densities of at least 5 g/L cell dry mass, preferably at least 10 g/L cell dry mass, or at least 15 g/L cell dry mass, e.g. exhibiting viabilities of more than 90% during standard sub-culture steps, preferably more than 95%.

In a growth phase, the carbon source is typically used in an excess or surplus amount, which is understood as an excess providing energy to increase the biomass, e.g. during the cultivation of a cell line with a high specific growth rate.

This surplus amount is particularly in excess of the limited amount of a carbon source as used under growth-limited conditions, to achieve a residual concentration in the fermentation broth that is measurable and typically at least 10-fold higher, preferably at least 50-fold or at least 100-fold higher than during feeding the cell culture with a medium containing limited carbon substrate.

The term "carbon substrate limited conditions" or "limited carbon source", herein also referred to as "supplemental carbon source", such as used according to the invention is herein understood to specifically refer to the type and amount of a carbon substrate facilitating the production of fermentation products by production cell lines, in particular in a cultivation process with controlled growth rates of less than the maximum growth rate. The production phase specifically follows a growth phase, e.g. in batch, fed-batch and continuous cultivation process.

Specifically preferred is a fed-batch process which is based on feeding of a growth limiting nutrient substrate to a culture. The fed-batch strategy is typically used in bio-industrial processes to reach a high cell density in the bioreactor. The controlled addition of the carbon substrate directly affects the growth rate of the culture and helps to avoid overflow metabolism or the formation of unwanted metabolic byproducts. Under carbon source limited conditions, the carbon source specifically may be contained in the feed of a fed-batch process. Thereby, the carbon substrate is provided in a limited amount.

Also in chemostat or continuous culture as described herein, the growth rate can be tightly controlled.

A "limited amount" of a carbon source is herein understood as the amount of a carbon source necessary to keep a production cell line under growth-limited conditions, e.g. in a production phase or production mode. Such a limited amount may be employed in a fed-batch process, where the carbon source is contained in a feed medium and supplied to the culture at low feed rates for sustained energy delivery, e.g. to produce a POI, while keeping the biomass at low specific growth rates. A feed medium is typically added to a fermentation broth during the production phase of a cell culture.

The limited amount of a carbon source may, for example, be determined by the residual amount of the carbon source in the cell culture broth, which is below a predetermined threshold or even below the detection limit as measured in a standard (carbohydrate) assay. The residual amount typically would be determined in the fermentation broth upon harvesting a fermentation product.

The limited amount of a carbon source may as well be determined by defining the average feed rate of the carbon source to the fermenter, e.g. as determined by the amount added over the full cultivation process, e.g. the fed-batch phase, per cultivation time, to determine a calculated average amount per time. This average feed rate is kept low to ensure complete usage of the supplemental carbon source by the cell culture, e.g. between 0.6 g $L^{-1}$ $h^{-1}$ (g carbon source per L initial fermentation volume and h time) and 25 g $L^{-1}$ $h^{-1}$, preferably between 1.6 g $L^{-1}$ $h^{-1}$ and 20 g $L^{-1}$ $h^{-1}$.

The limited amount of a carbon source may also be determined by measuring the specific growth rate, which specific growth rate is kept low, e.g. lower than the maximum specific growth rate, during the production phase, e.g. within a predetermined range, such as in the range of 0.001 $h^{-1}$ to 0.20 $h^{-1}$, or 0.02 $h^{-1}$ to 0.20 $h^{-1}$, preferably between 0.02 $h^{-1}$ and 0.15 $h^{-1}$.

Any type of organic carbon suitable used for eukaryotic cell culture may be used. According to a specific embodiment, the carbon source is a hexose such as glucose, fructose, galactose or mannose, a disaccharide, such as saccharose, an alcohol, such as glycerol or ethanol, or a mixture thereof.

According to a specifically preferred embodiment, the basal carbon source is selected from the group consisting of glucose, glycerol, ethanol, or mixtures thereof, and complex nutrient material. According to a preferred embodiment, the basal carbon source is glycerol.

According to a further specific embodiment, a supplemental carbon source is a hexose such as glucose, fructose, galactose and mannose, a disaccharide, such as saccharose, an alcohol, such as glycerol or ethanol, or a mixture thereof. According to a preferred embodiment, a supplemental carbon source is glucose.

Specifically, the method may employ glycerol as a basal carbon source and glucose as a supplemental carbon source.

Specifically, a feed medium as used herein is chemically defined and methanol-free.

The term "chemically defined" or "defined" with respect to cell culture medium, such as a minimal medium or feed medium in a fed-batch process, shall mean a cultivation medium suitable for the in vitro cell culture of a production cell line, in which all of the chemical components and (poly) peptides are known. Typically a chemically defined medium is entirely free of animal-derived components and represents a pure and consistent cell culture environment.

The term "cell line" as used herein refers to an established clone of a particular cell type that has acquired the ability to proliferate over a prolonged period of time. The term "host cell line" refers to a cell line as used for expressing an endogenous or recombinant gene or products of a metabolic pathway to produce polypeptides or cell metabolites mediated by such polypeptides. A "production host cell line" or "production cell line" is commonly understood to be a cell line ready-to-use for cultivation in a bioreactor to obtain the product of a production process, such as a POI. The term "eukaryotic host" or "eukaryotic cell line" shall mean any eukaryotic cell or organism, which may be cultivated to produce a POI or a host cell metabolite. It is well understood that the term does not include human beings.

According to specifically preferred eukaryotic host cells of the invention, the cell or cell line is selected from the group consisting of mammalian, insect, yeast, filamentous fungi and plant cell lines, preferably a yeast.

Specifically the yeast is selected from the group consisting of *Pichia, Candida, Torulopsis, Arxula, Hensenula, Yarrowia, Kluyveromyces, Saccharomyces, Komagataella*, preferably a methylotrophic yeast.

A specifically preferred yeast is *Pichia pastoris, Komagataella pastoris, K. phaffii*, or *K. pseudopastoris*.

The term "cell culture" or "cultivation", also termed "fermentation", with respect to a host cell line is meant the maintenance of cells in an artificial, e.g., an in vitro environment, under conditions favoring growth, differentiation or continued viability, in an active or quiescent state, of the cells, specifically in a controlled bioreactor according to methods known in the industry.

When cultivating a cell culture using the culture media of the present invention, the cell culture is brought into contact with the media in a culture vessel or with substrate under conditions suitable to support cultivation of the cell culture. In certain embodiments, a culture medium as described herein is used to culture cells according to standard cell culture techniques that are well-known in the art. In various aspects of the invention, a culture medium is provided that can be used for the growth of eukaryotic cells, specifically yeast or filamentous fungi.

Cell culture media provide the nutrients necessary to maintain and grow cells in a controlled, artificial and in vitro environment. Characteristics and compositions of the cell culture media vary depending on the particular cellular requirements. Important parameters include osmolality, pH, and nutrient formulations. Feeding of nutrients may be done in a continuous or discontinuous mode according to methods known in the art. The culture media used according to the invention are particularly useful for producing recombinant proteins.

Whereas a batch process is a cultivation mode in which all the nutrients necessary for cultivation of the cells are contained in the initial culture medium, without additional supply of further nutrients during fermentation, in a fed-batch process, after a batch phase, a feeding phase takes place in which one or more nutrients are supplied to the culture by feeding. The purpose of nutrient feeding is to increase the amount of biomass in order to increase the amount of recombinant protein as well. Although in most cultivation processes the mode of feeding is critical and important, the present invention employing the promoter of the invention is not restricted with regard to a certain mode of cultivation.

In certain embodiments, the method of the invention is a fed-batch process. Specifically, a host cell transformed with a nucleic acid construct encoding a desired recombinant POI, is cultured in a growth phase medium and transitioned to a production phase medium in order to produce a desired recombinant POI.

The feed medium may be added to the culture medium in the liquid form or else in an alternative form, such as a solid, e.g. as a tablet or other sustained release means, or a gas, e.g. carbon dioxide. Yet, according to a preferred embodiment the limited amount of a supplemental carbon source added to the cell culture medium, may even be zero. Preferably, under conditions of a limited carbon substrate, the concentration of a supplemental carbon source in the culture medium is 0-1 g/L, preferably less than 0.6 g/L, more preferred less than 0.3 g/L, more preferred less than 0.1 g/L, preferably 1-50 mg/L, more preferred 1-10 mg/L, specifically preferred 1 mg/L or even below, such as below the detection limit as measured with a suitable standard assay, e.g. determined as a residual concentration in the culture medium upon consumption by the growing cell culture.

In a preferred method, the limited amount of the carbon source provides for a residual amount in the cell culture which is below the detection limit as determined in the fermentation broth at the end of a production phase or in the output of a fermentation process, preferably upon harvesting the fermentation product.

Preferably, the limited amount of a supplemental carbon source is growth limiting to keep the specific growth rate lower than the maximum specific growth rate, such as in the range of $0.001\ h^{-1}$ to $0.20\ h^{-1}$, or $0.02\ h^{-1}$ to $0.20\ h^{-1}$, preferably between $0.02\ h^{-1}$ and $0.15\ h^{-1}$.

In another embodiment, host cells of the present invention are cultivated in continuous mode, e.g. a chemostat. A continuous fermentation process is characterized by a defined, constant and continuous rate of feeding of fresh culture medium into the bioreactor, whereby culture broth is at the same time removed from the bioreactor at the same defined, constant and continuous removal rate. By keeping culture medium, feeding rate and removal rate at the same constant level, the cultivation parameters and conditions in the bioreactor remain constant.

A stable cell culture as described herein is specifically understood to refer to a cell culture maintaining the genetic properties, specifically keeping the POI production level high, e.g. at least at a µg level, even after about 20 generations of cultivation, preferably at least 30 generations, more preferably at least 40 generations, most preferred of at least 50 generations. Specifically, a stable recombinant host cell line is provided which is considered a great advantage when used for industrial scale production.

The cell culture of the invention is particularly advantageous for methods on an industrial manufacturing scale, e.g. with respect to both the volume and the technical system, in combination with a cultivation mode that is based on feeding of nutrients, in particular a fed-batch or batch process, or a continuous or semi-continuous process (e.g. chemostat).

The term "expression" or "expression system" or "expression cassette" refers to nucleic acid molecules containing a desired coding sequence and control sequences in operable linkage, so that hosts transformed or transfected with these sequences are capable of producing the encoded proteins or host cell metabolites. In order to effect transformation, the expression system may be included in a vector; however, the relevant DNA may also be integrated into the host chromosome. Expression may refer to secreted or non-secreted expression products, including polypeptides or metabolites.

"Expression constructs" or "vectors" or "plasmid" used herein are defined as DNA sequences that are required for the transcription of cloned recombinant nucleotide sequences, i.e. of recombinant genes and the translation of their mRNA in a suitable host organism. Expression vectors or plasmids usually comprise an origin for autonomous replication in the host cells, selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences.

The expression construct of the invention specifically comprises a promoter of the invention, operably linked to a nucleotide sequence encoding a POI under the transcriptional control of said promoter, which promoter is not natively associated with the coding sequence of the POI.

The term "heterologous" as used herein with respect to a nucleotide or amino acid sequence or protein, refers to a compound which is either foreign, i.e. "exogenous", such as not found in nature, to a given host cell; or that is naturally found in a given host cell, e.g., is "endogenous", however, in the context of a heterologous construct, e.g. employing a heterologous nucleic acid. The heterologous nucleotide sequence as found endogenously may also be produced in an unnatural, e.g. greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence is understood to be heterologous. An example of a heterologous polynucleotide is a nucleotide sequence not natively associated with the promoter according to the invention, e.g. to obtain a hybrid promoter, or operably linked to a coding sequence, as described herein. As a result, a hybrid or chimeric polynucleotide may be obtained. A further example of a heterologous compound is a POI encoding polynucleotide operably linked to a transcriptional control element, e.g., a promoter of the invention, to which an endogenous, naturally-occurring POI coding sequence is not normally operably linked.

The term "variant" as used herein in the context of the present invention shall specifically refer to any sequence derived from a parent sequence, e.g. by size variation, e.g. elongation or fragmentation, mutation, hybridization (including combination of sequences), or with a specific degree of homology, or analogy.

The invention specifically provides for a promoter which is a wild-type promoter, e.g. of *P. pastoris*, or a functionally active variant thereof, e.g. capable of controlling the transcription of a specific gene in a wild-type or recombinant eukaryotic cell.

The functionally active variant promoter may e.g. be derived from the promoter sequence pCS1 (SEQ ID NO:1) by mutagenesis, thus employing the pCS1 sequence as a "parent" sequence, to produce sequences suitable for use as a promoter in recombinant cell lines. Such variant promoter may be obtained from a (pCS1) library of mutant sequences by selecting those library members with predetermined properties. Variant promoters may have the same or even improved properties, e.g. improved in promoter strength to support POI production, still with substantially the same promoter function and strength at high and low growth rates, specifically understood herein as "growth-rate independent function".

The variant promoter may also be derived from analogous sequences, e.g. from eukaryotic species other than *Pichia pastoris* or from a genus other than *Pichia*, such as from *K. lactis, Z. rouxii, P. stipitis, H. polymorpha*. Specifically, the analogous promoter sequences natively associated with genes analogous to the corresponding *P. pastoris* genes may be used as such or as parent sequences to produce functionally active variants thereof. Specifically, a promoter analogous to pCS1 is characterised that it is natively associated with a gene analogous to CS1 (see amino acid sequence of SEQ ID NO:9 or 11). The properties of such analogous promoter sequences or functionally active variants thereof may be determined using standard techniques.

The "functionally active" variant of a nucleotide or promoter sequence as used herein specifically means a mutant sequence, e.g. resulting from modification of a parent sequence by insertion, deletion or substitution of one or more nucleotides within the sequence or at either or both of the distal ends of the sequence, and which modification does not affect (in particular impair) the activity of this sequence.

Specifically, the functionally active variant of the promoter sequence according to the invention is selected from the group consisting of homologs with at least about 60% nucleotide sequence identity, preferably at least 70%, at least 80%, or at least 90% degree of homology or sequence identity to the parent sequence; and/or homologs obtainable by modifying the parent nucleotide sequence, such as the pCS1 sequence or the sequence of a size variant used as a template to provide for mutations, e.g. by insertion, deletion or substitution of one or more nucleotides within the sequence or at either or both of the distal ends of the sequence, preferably with (i.e. comprising or consisting of) a nucleotide sequence of 80 bp to 1500 bp, preferably at least 100 bp, at least 200 bp, preferably at least 300 bp, more preferred at least 400 bp, at least 500 bp, at least 600 bp, at least 700 bp, at least 800 bp, at least 900 bp, or at least 1000 bp; and analogs derived from species other than *Pichia pastoris*.

Specifically preferred functionally active variants are those derived from a promoter according to the invention by modification, extension and/or fragments of the promoter sequence, with (i.e. comprising or consisting of) a nucleotide sequence of at least 80 bp, preferably at least 100 bp, preferably at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp, preferably up to 1500 bp.

A functionally active variant of a parent promoter sequences as described herein may specifically obtained through mutagenesis methods. The term "mutagenesis" as used in the context of the present invention shall refer to a method of providing mutants of a nucleotide sequence, e.g. through insertion, deletion and/or substitution of one or more nucleotides, so to obtain variants thereof with at least one change in the non-coding or coding region. Mutagenesis may be through random, semi-random or site directed mutation. Typically large randomized gene libraries are produced with a high gene diversity, which may be selected according to a specifically desired genotype or phenotype.

Some of the preferred functionally active variants of the promoter according to the invention are size variants or specifically fragments of pCS1, preferably those including the 3' end of a promoter nucleotide sequence, e.g. a nucleotide sequence derived from one of the promoter nucleotide sequences which has of a specific length and insertions or a deletion of the 5' terminal region, e.g. an elongation or cut-off of the nucleotide sequence at the 5' end, so to obtain a specific length with a range from the 3' end to a varying 5' end, such as with a length of the nucleotide sequence of at least 80 bp, preferably at least 100 bp, preferably at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp.

The elongated size variant of the invention preferably comprises additional one or more nucleotide(s) at the 5' end of the pCS1 sequence, e.g. those which are natively associated with the wild-type pCS1 sequence in the cell of origin.

For example, a functionally active variant of pCS1 may comprise a nucleotide sequence or consist of a nucleotide sequence selected from the group consisting of pCS1a (SEQ ID NO:2), pCS1b (SEQ ID NO:3), pCS1c (SEQ ID NO:4), pCS1d (SEQ ID NO:5), pCS1e (SEQ ID NO:6), pCS1f (SEQ ID NO:7), and pCS1g (SEQ ID NO:8), thus, a nucleotide sequence within the range of 80-1500 bp.

The functionally active variant of a promoter of the invention is also understood to encompass hybrids of the pCS1 or any of the functionally active variants thereof, in particular any of the parent size variant or fragment sequences, e.g. resulting from combination with one or more of any of the sequences that qualify as pCS1 or functionally active variants thereof, e.g. at least two of such parent sequences, at least 3, at least 4 or at least 5 of the sequences, e.g. a combination of two or more of the pCS1 elongated sequences or fragments selected from the group consisting of pCS1a, pCS1b, pCS1c, pCS1d, pCS1e, pCS1f, and pCS1g. In another embodiment, the hybrid is composed of at least one of the sequences selected from pCS1 or any of the functionally active variants thereof, in particular any of the size variant or fragment sequences, and a heterologous sequences which is e.g. not natively associated with the pCS1 sequence in *P. pastoris*.

The functionally active variant of a promoter of the invention is further understood to encompass a nucleotide sequence which hybridizes under stringent conditions to the pCS1 promoter or any of the functionally active size variants or fragments, mutants or hybrid nucleic acid sequences thereof.

As used in the present invention, the term "hybridization" or "hybridizing" is intended to mean the process during which two nucleic acid sequences anneal to one another with stable and specific hydrogen bonds so as to form a double strand under appropriate conditions. The hybridization between two complementary sequences or sufficiently complementary sequences depends on the operating conditions that are used, and in particular the stringency. The stringency may be understood to denote the degree of homology; the higher the stringency, the higher percent homology between the sequences. The stringency may be defined in particular by the base composition of the two nucleic sequences, and/or by the degree of mismatching between these two nucleic sequences. By varying the conditions, e.g. salt concentration and temperature, a given nucleic acid sequence may be allowed to hybridize only with its exact complement (high stringency) or with any somewhat related sequences (low stringency). Increasing the temperature or decreasing the salt concentration may tend to increase the selectivity of a hybridization reaction.

As used in the present invention the phrase "hybridizing under stringent hybridizing conditions" is preferably understood to refer to hybridizing under conditions of certain stringency. In a preferred embodiment the "stringent hybridizing conditions" are conditions where homology of the two nucleic acid sequences is at least 70%, preferably at least 80%, preferably at least 90%, i.e. under conditions where hybridization is only possible if the double strand obtained during this hybridization comprises preferably at least 70%, preferably at least 80%, preferably at least 90% of A-T bonds and C-G bonds.

The stringency may depend on the reaction parameters, such as the concentration and the type of ionic species present in the hybridization solution, the nature and the concentration of denaturing agents and/or the hybridization temperature. The appropriate conditions can be determined by those skilled in the art, e.g. as described in Sambrook et al. (Molecular Cloning: A Laboratory Manual, Cold Spring Harbor, 1989).

The functionally active variant of the invention is specifically characterized by exhibiting substantially the same activity as pCS1.

The term "substantially the same activity" as used herein specifically refers to the activity as indicated by substantially the same or improved promoter strength, specifically the expression or transcriptional strength of the promoter, and its substantially the same or improved characteristics with respect to the promoter strength, specifically determined independent of the growth rate of the host cell such as an expression or transcriptional strength substantially the same as pCS1, e.g. +/−20% or +/−10%, and/or higher than the native pGAP promoter of the host cell, e.g. an at least 1.1-fold increase, or an at least 1.2-fold increase, preferably at least 1.3-fold, preferably at least 1.4-fold, preferably at least 1.5-fold, preferably at least 1.6-fold, preferably at least 1.7-fold, preferably at least 1.8-fold, preferably at least 1.9-fold, and preferably at least 2-fold increase relative to the pGAP promoter strength, or even higher, e.g. at least 3-fold, at least 4-fold, at least 5-fold, at least 10-fold, or at least up to a 15-fold activity, as determined in a suitable test system employing the same type of a host cell, the same cultivation conditions and the same nucleic acid encoding an expression product such as a POI.

The term "homology" indicates that two or more nucleotide sequences have the same or conserved base pairs at a corresponding position, to a certain degree, up to a degree close to 100%. A homologous sequence of the invention typically has at least about 60% nucleotide sequence identity, preferably at least about 70% identity, more preferably at least about 80% identity, more preferably at least about 90% identity, more preferably at least about 95% identity, more preferably at least about 98% or 99% identity.

The homologous promoter sequence according to the invention preferably has a certain homology to any of the pCS1, pCS1a, pCS1b, pCS1c, pCS1d, pCS1e, pCS1f, and pCS1g promoter nucleotide sequences of *P. pastoris* in at least specific parts of the nucleotide sequence, such as including the 3' region of the respective promoter nucleotide sequence, preferably a part with a specific length up to the 3' end of the respective promoter nucleotide sequence, such as a part with a length of 80 bp to 1500 bp, preferably at least 100 bp, preferably at least 200 bp, preferably at least 300 bp, more preferred at least 400 bp, at least 500 bp, at least 600 bp, at least 700 bp, at least 800 bp, at least 900 bp, or at least 1000 bp, and analogs derived from species other than *Pichia pastoris*. Specifically at least those parts are preferably homologous within the range of 300-1000 bp, including the 3' terminal sequence of the respective promoter nucleotide sequence.

Analogous sequences are typically derived from other species or strains. It is expressly understood that any of the analogous promoter sequences of the present invention that are derived from species other than *Pichia pastoris* may comprise a homologous sequence, i.e. a sequence with a certain homology as described herein. Thus, the term "homologous" may also include analogous sequences. On the other hand, it is understood that the invention also refers to analogous sequences and homologs thereof that comprise a certain homology.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "isolated" or "isolation" as used herein with respect to a nucleic acid, a POI or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized. With reference to nucleic acids of the invention, the term "isolated nucleic acid" or "isolated nucleic acid sequence" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Specifically, the term "isolated nucleic acid" according to the invention excludes that the pCS1 sequence is linked to a nucleic acid encoding the CS1 protein. An "isolated nucleic acid" (either DNA or RNA) may further represent a molecule produced directly by biological or synthetic means and separated from other components present during its production.

The term "operably linked" as used herein refers to the association of nucleotide sequences on a single nucleic acid molecule, e.g. a vector, in a way such that the function of one or more nucleotide sequences is affected by at least one other nucleotide sequence present on said nucleic acid molecule. For example, a promoter is operably linked with a coding sequence of a recombinant gene, when it is capable of effecting the expression of that coding sequence. As a further example, a nucleic acid encoding a signal peptide is operably linked to a nucleic acid sequence encoding a POI, when it is capable of expressing a protein in the secreted form, such as a preform of a mature protein or the mature protein. Specifically such nucleic acids operably linked to each other may be immediately linked, i.e. without further elements or nucleic acid sequences in between the nucleic acid encoding the signal peptide and the nucleic acid sequence encoding a POI.

The term "promoter" as used herein refers to a DNA sequence capable of controlling the expression of a coding sequence or functional RNA. Promoter activity may be assessed by its transcriptional efficiency. This may be determined directly by measurement of the amount of mRNA transcription from the promoter, e.g. by Northern Blotting or indirectly by measurement of the amount of gene product expressed from the promoter.

The promoter of the invention specifically initiates, regulates, or otherwise mediates or controls the expression of a coding DNA. Promoter DNA and coding DNA may be from the same gene or from different genes, and may be from the same or different organisms.

The promoter of the invention is specifically understood as a constitutive promoter, i.e. a promoter which controls expression without the need for induction, or the possibility of repression. Therefore, there is continuous and steady expression at a certain level. Because of the unique function of high promoter strength at all growth phases or growth rates of the host cell, the constitutive promoter of the invention is particularly useful in a fed-batch culture of the host cell line. Constitutive promoters of the prior art had the disadvanatage of low strength at growth-limited conditions, e.g. in fed-batch processes, or were used in embodiments where the host cells were maintained at a high growth rate, e.g. in the mid-exponential phase.

The strength of the promoter of the invention specifically refers to its transcription strength, represented by the efficiency of initiation of transcription occurring at that promoter with high or low frequency. The higher transcription strength the more frequently transcription will occur at that promoter. Promoter strength is important, because it determines how often a given mRNA sequence is transcribed, effectively giving higher priority for transcription to some genes over others, leading to a higher concentration of the transcript. A gene that codes for a protein that is required in large quantities, for example, typically has a relatively strong promoter. The RNA polymerase can only perform one transcription task at a time and so must prioritize its work to be efficient. Differences in promoter strength are selected to allow for this prioritization. According to the invention the promoter is relatively strong independent of the metabolism or the growth rate of the host cell, e.g. both, during in phases of high and low growth rates of a cell culture and specifically independent of the carbon source, exhibiting a state of about maximal activity, specifically at about a constant level.

The relative strength is commonly determined with respect to a standard promoter, such as the respective pGAP promoter of the cell used as the host cell. The frequency of transcription is commonly understood as the transcription rate, e.g. as determined by the amount of a transcript in a suitable assay, e.g. RT-PCR or Northern blotting. The strength of a promoter to express a gene of interest is commonly understood as the expression strength or the capability of support a high expression level/rate. For example, the expression and/or transcription strength of a promoter of the invention is determined in the host cell which is *P. pastoris* and compared to the native pGAP promoter of *P. pastoris*.

The transcription rate may be determined by the transcription strength on a microarray, or with qantitative real time PCR (qRT-PCR) where microarray or qRT-PCR data show the difference of expression level between conditions with high growth rate and conditions with low growth rate, or conditions employing different media composition, and a high signal intensity as compared to the native pGAP promoter. A suitable test system is specifically described in Example 11 below.

The promoter of the invention exerts a relatively high transcription strength, reflected by a transcription rate or transcription strength of at least 110% as compared to the native pGAP promoter in the host cell, sometimes called "homologous pGAP promoter". Preferably the transcription rate or strength is at least 110%, preferably at least 120%, or at least 130%, in specifically preferred cases at least 140%, at least 150%, at least 160%, at least 170%, at least 180%, at least 190%, at least 200%, at least about 3-fold, at least about 4-fold, at least about 5-fold, at least about 10-fold, or at least about 15-fold, or even higher as compared to the native pGAP promoter, e.g. determined in the eukaryotic cell selected as host cell for producing the POI, such as determined under carbon substrate rich conditions, e.g. batch cultures, or under carbon substrate limited conditions, e.g. chemostat or fed batch cultivations.

Preferably the transcription analysis is quantitive or semi-quantitative, preferably employing qRT-PCR, DNA microarrays, RNA sequencing and transcriptome analysis.

The expression rate may, for example, be determined by the amount of expression of a reporter gene, such as eGFP, e.g. as described in the Example section below, a test system is specifically described in Example 10. It could be shown that the pCS1 promoter has a relatively high transcription rate of at least 110% as compared to the native pGAP promoter, upon cultivating a clone in solution.

The promoter of the invention exerts relatively high expression strength, reflected by an expression level of gene of interest, which is at least 110% as compared to the native pGAP promoter in the host cell, sometimes called "homologous pGAP promoter". Preferably the expression strength is at least 110%, preferably at least 120%, or at least 130%, in specifically preferred cases at least 140%, at least 150%, at least 160%, at least 170%, at least 180%, at least 190%, at least 200%, at least about 3-fold, at least about 4-fold, at least about 5-fold, at least about 10-fold, or at least about 15-fold, or even higher as compared to the native pGAP promoter, e.g. determined in the eukaryotic cell selected as host cell for producing the POI, such as determined under carbon substrate rich conditions, e.g. batch cultures, or under carbon substrate limited conditions, e.g. chemostat or fed batch cultivations.

The native pGAP promoter initiates expression of the gap gene encoding glyceraldehyde-3-phosphate dehydrogenase (GAPDH), which is a constitutive promoter present in most living organisms. GAPDH (EC 1\2\1\12), a key enzyme of glycolysis and gluconeogenesis, plays a crucial role in catabolic and anabolic carbohydrate metabolism. Therefore, the pGAP promoter, though understood to be a constitutive (such as non-inducible by feeding with specific carbon sources) promoter, is a metabolic promoter that exerts increasing promoter strength with increasing growth rate. Therefore, the pGAP promoter is hardly suitable in an efficient production process during the cultivation of the host cell line in phases that are characterized by a low growth rate.

In contrast, the promoter of the invention surprisingly maintains its high promoter strength (essentially) at a constantly high transcript level at all growth phases of a host cell culture.

The native pGAP promoter specifically is active in a recombinant eukaryotic cell in a similar way as in a native eukaryotic cell of the same species or strain, including the unmodified (non-recombinant) or recombinant eukaryotic cell. Such native pGAP promoter is commonly understood to be an endogenous promoter, thus, homologous to the eukaryotic cell, and serves as a standard or reference promoter for comparison purposes.

For example, a native pGAP promoter of *P. pastoris* is the unmodified, endogenous promoter sequence in *P. pastoris*, as used to control the expression of GAPDH in *P. pastoris*, e.g. having the sequence shown in FIG. 3: native pGAP promoter sequence of *P. pastoris* (GS115) (SEQ ID NO:13). If *P. pastoris* is used as a host for producing a POI according to the invention, the transcription strength or rate of the promoter according to the invention is compared to such native pGAP promoter of *P. pastoris*.

As another example, a native pGAP promoter of *S. cerevisiae* is the unmodified, endogenous promoter sequence in *S. cerevisiae*, as used to control the expression of GAPDH in *S. cerevisiae*. If *S. cerevisiae* is used as a host for producing a POI according to the invention, the transcription strength or rate of the promoter according to the invention is compared to such native pGAP promoter of *S. cerevisiae*.

Therefore, the relative expression or transcription strength of a promoter according to the invention is usually compared to the native pGAP promoter of a cell of the same species or strain that is used as a host for producing a POI.

It is specifically understood that the promoter of the invention is preferably not a metabolic promoter such as for example a promoter naturally operably linked to a gene encoding an abundant glycolytic enzyme or an enzyme of gluconeogenesis, a ribosomal protein or an enzyme such as an intracellular protease or a protease being secreted from the host cell.

Specifically preferred is a promoter of the invention, which has at least an expression strength or transcription strength of pCS1. The comparative promoter strength employing the pGAP promoter as a reference may be determined by standard means, such as by measuring the quantity of expression products or the quantity of transcripts, e.g. employing a microarray, Northern Blot, RNA sequencing or qRT-PCR, or else in a cell culture, such as by measuring the quantity of respective gene expression products in recombinant cells. Exemplary tests are illustrated in the Examples section.

The term "protein of interest (POI)" as used herein refers to a polypeptide or a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. In some cases the term POI as used herein also refers to any metabolite product by the host cell as mediated by the recombinantly expressed protein.

Specifically, the POI as described herein is a eukaryotic protein, preferably a mammalian protein, specifically a protein heterologous to the host cell.

A POI produced according to the invention may be a multimeric protein, preferably a dimer or tetramer.

According to one aspect of the invention, the POI is a recombinant or heterologous protein, preferably selected from therapeutic proteins, including antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI.

A specific POI is an antigen binding molecule such as an antibody, or a fragment thereof. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH or VHH or V-NAR.

According to a specific embodiment, a fermentation product is manufactured using the POI, a metabolite or a derivative thereof.

The POI may specifically be recovered from the cell culture in the purified form, e.g. substantially pure.

The term "substantially pure" or "purified" as used herein shall refer to a preparation comprising at least 50% (w/w), preferably at least 60%, 70%, 80%, 90% or 95% of a compound, such as a nucleic acid molecule or a POI. Purity is measured by methods appropriate for the compound (e.g. chromatographic methods, polyacrylamide gel electrophoresis, HPLC analysis, and the like).

The term "recombinant" as used herein shall mean "being prepared by or the result of genetic engineering". Thus, a "recombinant microorganism" comprises at least one "recombinant nucleic acid". A recombinant microorganism specifically comprises an expression vector or cloning vector, or it has been genetically engineered to contain a recombinant nucleic acid sequence. A "recombinant protein" is produced by expressing a respective recombinant nucleic acid in a host. A "recombinant promoter" is a genetically engineered non-coding nucleotide sequence suitable for its use as a functionally active promoter as described herein.

Therefore, a new promoter was identified with unique functional properties. Unexpectedly, PAS_chr1-4 (herein called CS1 gene, SEQ ID NO:9) was identified by analysis of transcription strength in production process conditions as the strongest transcribed gene in *P. pastoris*. The encoded CS1 protein (SEQ ID NO:10) is not a glycolytic enzyme or protein, but predicted to be located on the cell surface via a GPI-anchor. Though the 9.43 Mbp genomic sequence of the GS115 strain of *P. pastoris* has been determined and disclosed in US20110021378A1, the properties of individual sequences, such as promoter sequences, have not been investigated in detail.

It was surprising that such promoter could be effectively used according to the invention. *Pichia* promoters of the prior art such as used in industrial scale POI production were mainly derived from the methanol metabolic pathway and needed the addition of methanol to induce POI production, which is often not desired. The promoter and method according to the invention has the advantage that it may provide for an increased production by an enhanced expression, and has the reduced risk of contamination due to the specific promoter regulation, in particular when using a chemically defined medium, free of methanol.

It turned out that the promoter according to the invention would exert its improved activity mainly independent of a suitable carbon substrate amount and specific culture media. As an example, *P. pastoris* could be successfully cultivated under conditions of an industrial production process. First a batch culture on a basal carbon source, such as glycerol, was employed, followed by a fed batch with limited feed of a supplemental carbon source, such as glucose. Samples were taken close to the end of the first batch phase, and in limited growth conditions, e.g. using a limited amount of supplemental carbon source. Transcriptome analysis with DNA micoarrays revealed specific genes that are strongly active on the supplemental carbon source and in the presence of surplus carbon, i.e. the basal carbon source in excess amount. The pCS1 promoter sequence was identified as surprisingly strong promoter at high and low growth rates. The comparable pGAP promoter of the prior art was significantly weaker.

The features of strong recombinant gene expression on the basal carbon source, and strong expression on limited supplemental carbon source, could be verified in fermentation processes.

The nucleotide sequences that could be used as constitutive promoter sequences according to the invention, would provide for an improved recombinant protein production, can be obtained from a variety of sources. The origin of the promoter according to the invention is preferably from a yeast cell, most preferably from methylotrophic yeast such as from the *Pichia* genus or from the *P. pastoris* species, which promoter may then be used as a parent sequence to produce suitable variants, e.g. mutants or analogs.

It is contemplated that a series of yeast cells, in particular of *Pichia* strains, may be suitable to obtain respective promoter sequences or respective analogs in different species.

Variants of the identified *P. pastoris* promoter, including functionally active variants, such as homologs and analogs may be produced employing standard techniques. The promoter may e.g. be modified to generate promoter variants with altered expression levels and regulatory properties.

For instance, a promoter library may be prepared by mutagenesis of the promoter sequences according to the invention, which may be used as parent molecules, e.g. to fine-tune the gene expression in eukaryotic cells by analysing variants for their expression under different fermentation strategies and selecting suitable variants. A synthetic library of variants may be used, e.g. to select a promoter matching the requirements for producing a selected POI. Such variants may have increased expression efficiency in eukaryotic host cells and high expression under carbon source rich and limiting conditions.

The differential fermentation strategies would distinguish between a growth phase and a production phase. Growth and/or production can suitably take place in batch mode, fed-batch mode or continuous mode. Any suitable bioreactor can be used, including batch, fed-batch, continuous, stirred tank reactor, or airlift reactor.

It is advantageous to provide for the fermentation process on a pilot or industrial scale. The industrial process scale would preferably employ volumina of at least 10 L, specifically at least 50 L, preferably at least 1 $m^3$, preferably at least 10 $m^3$, most preferably at least 100 $m^3$.

Production conditions in industrial scale are preferred, which refer to e.g. fed batch cultivation in reactor volumes of 100 L to 10 $m^3$ or larger, employing typical process times of several days, or continuous processes in fermenter volumes of approximately 50-1000 L or larger, with dilution rates of approximately 0.02-0.15 $h^{-1}$.

The suitable cultivation techniques may encompass cultivation in a bioreactor starting with a batch phase, followed by a short exponential fed batch phase at high specific growth rate, further followed by a fed batch phase at a low specific growth rate. Another suitable cultivation technique may encompass a batch phase followed by a continuous cultivation phase at a low dilution rate.

A preferred embodiment of the invention includes a batch culture to provide biomass followed by a fed-batch culture for high yields POI production.

It is preferred to cultivate the host cell line according to the invention in a bioreactor under growth conditions to obtain a cell density of at least 1 g/L cell dry weight, more preferably at least 10 g/L cell dry weight, preferably at least 20 g/L cell dry weight. It is advantageous to provide for such yields of biomass production on a pilot or industrial scale.

A growth medium allowing the accumulation of biomass, specifically a basal growth medium, typically comprises a carbon source, a nitrogen source, a source for sulphur and a source for phosphate. Typically, such a medium comprises furthermore trace elements and vitamins, and may further comprise amino acids, peptone or yeast extract.

Preferred nitrogen sources include $NH_4H_2PO_4$, or $NH_3$ or $(NH_4)_2SO_4$,

Preferred sulphur sources include $MgSO_4$, or $(NH_4)_2SO_4$ or $K_2SO_4$,

Preferred phosphate sources include $NH_4H_2PO_4$, or $H_3PO_4$ or $NaH_2PO_4$, $KH_2PO_4$, $Na_2HPO_4$ or $K_2HPO_4$;

Further typical medium components include KCl, $CaCl_2$, and Trace elements such as: Fe, Co, Cu, Ni, Zn, Mo, Mn, I, B;

Preferably the medium is supplemented with vitamin $B_7$;

A typical growth medium for *P. pastoris* comprises glycerol, sorbitol or glucose, $NH_4H_2PO_4$, $MgSO_4$, KCl, $CaCl_2$, biotin, and trace elements.

In the production phase a production medium is specifically used with only a limited amount of a supplemental carbon source.

Preferably the host cell line is cultivated in a mineral medium with a suitable carbon source, thereby further simplifying the isolation process significantly. An example of a preferred mineral medium is one containing an utilizable carbon source (e.g. glucose, glycerol, sorbitol or methanol), salts containing the macro elements (potassium, magnesium, calcium, ammonium, chloride, sulphate, phosphate) and trace elements (copper, iodide, manganese, molybdate, cobalt, zinc, and iron salts, and boric acid), and optionally vitamins or amino acids, e.g. to complement auxotrophies.

The cells are cultivated under conditions suitable to effect expression of the desired POI, which can be purified from the cells or culture medium, depending on the nature of the expression system and the expressed protein, e.g. whether the protein is fused to a signal peptide and whether the protein is soluble or membrane-bound. As will be understood by the skilled artisan, cultivation conditions will vary according to factors that include the type of host cell and particular expression vector employed.

By selecting the suitable promoter sequence according to the invention, optionally in combination with further preferred regulatory sequences, it is possible to provide for, under comparable conditions, at least the same, or at least about an 1.1-fold, or at least about 1.2-fold, at least about 1.5-fold, at least about 2-fold, at least about 3-fold, at least about 4-fold, at least about 5-fold, at least about 10-fold, or at least up to about a 15-fold activity, e.g. under growth-limited conditions in a fed-batch process, as represented by the promoter activity or transcription strength, or regulated by the promoter strength relative to a GAP promoter that is homologous to the production cell, a native pGAP, or isolated from *P. pastoris*.

A typical production medium comprises a supplemental carbon source, and further $NH_4H_2PO_4$, $MgSO_4$, KCl, $CaCl_2$, biotin, and trace elements.

For example the feed of the supplemental carbon source added to the fermentation may comprise a carbon source with up to 50 wt % utilizable sugars. The low feed rate of the supplemental medium will limit the effects of product or byproduct inhibition on the cell growth, thus a high product yield based on substrate provision will be possible.

The fermentation preferably is carried out at a pH ranging from 3 to 7.5.

Typical fermentation times are about 24 to 120 hours with temperatures in the range of 20° C. to 35° C., preferably 22-30° C.

In general, the recombinant nucleic acids or organisms as referred to herein may be produced by recombination techniques well known to a person skilled in the art. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual, Cold Spring Harbor, (1982).

According to a preferred embodiment of the present invention, a recombinant construct is obtained by ligating the promoter and relevant genes into a vector or expression construct. These genes can be stably integrated into the host cell genome by transforming the host cell using such vectors or expression constructs.

Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector.

Appropriate expression vectors typically comprise further regulatory sequences suitable for expressing DNA encoding a POI in a eukaryotic host cell. Examples of regulatory sequences include operators, enhancers, ribosomal binding sites, and sequences that control transcription and translation initiation and termination. The regulatory sequences may be operably linked to the DNA sequence to be expressed.

To allow expression of a recombinant nucleotide sequence in a host cell, the expression vector may provide the promoter according to the invention adjacent to the 5' end of the coding sequence, e.g. upstream from the GOI or a signal peptide gene enabling secretion of the POI. The transcription is thereby regulated and initiated by this promoter sequence.

A signal peptide may be a heterologous signal peptide or a hybrid of a native and a heterologous signal peptide, and may specifically be heterologous or homologous to the host organism producing the protein. The function of the signal peptide is to allow the POI to be secreted to enter the endoplasmatic reticulum. It is usually a short (3-60 amino acids long) peptide chain that directs the transport of a protein outside the plasma membrane, thereby making it easy to separate and purify the heterologous protein. Some signal peptides are cleaved from the protein by signal peptidase after the proteins are transported.

Exemplary signal peptides are signal sequences from *S. cerevisiae* alpha-mating factor prepro peptide and the signal peptide from the *P. pastoris* acid phosphatase gene (PHO1).

A promoter sequence is understood to be operably linked to a coding sequence, if the promotor controls the transcription of the coding sequence. If a promoter sequence is not natively associated with the coding sequence, its transcription is either not controlled by the promoter in native (wild-type) cells or the sequences are recombined with different contiguous sequences.

To prove the function of the relevant sequences, expression vectors comprising one or more of the regulatory elements may be constructed to drive expression of a POI, and the expressed yield is compared to constructs with conventional regulatory elements. A detailed description of the experimental procedure can be found in the examples below. The identified genes may be amplified by PCR from *P. pastoris* using specific nucleotide primers, cloned into an expression vector and transformed into a eukaryotic cell line, e.g. using a yeast vector and a strain of *P. pastoris*, for high level production of various different POI. To estimate the effect of the promoter according to the invention on the amount of recombinant POI so produced, the eukaryotic cell line may be cultured in shake flask experiments and fedbatch or chemostat fermentations in comparison with strains comprising a conventional constitutive, e.g. a growth-dependent promoter, such as for example the standard pGAP promoter in the respective cell. In particular, the choice of the promoter has a great impact on the recombinant protein production.

The POI can be produced using the recombinant host cell line by culturing a transformant, thus obtained in an appropriate medium, isolating the expressed product or metabolite from the culture, and optionally purifying it by a suitable method.

Transformants according to the present invention can be obtained by introducing such a vector DNA, e.g. plasmid DNA, into a host and selecting transformants which express the POI or the host cell metabolite with high yields. Host cells are treated to enable them to incorporate foreign DNA by methods conventionally used for transformation of eukaryotic cells, such as the electric pulse method, the protoplast method, the lithium acetate method, and modified methods thereof. *P. pastoris* is preferably transformed by electroporation. Preferred methods of transformation for the uptake of the recombinant DNA fragment by the microorganism include chemical transformation, electroporation or transformation by protoplastation. Transformants according to the present invention can be obtained by introducing such a vector DNA, e.g. plasmid DNA, into a host and selecting transformants which express the relevant protein or host cell metabolite with high yields.

Several different approaches for the production of the POI according to the method of the invention are preferred. Substances may be expressed, processed and optionally secreted by transforming a eukaryotic host cell with an expression vector harbouring recombinant DNA encoding a relevant protein and at least one of the regulatory elements as described above, preparing a culture of the transformed cell, growing the culture, inducing transcription and POI production, and recovering the product of the fermentation process.

The host cell according to the invention is preferably tested for its expression capacity or yield by the following test: ELISA, activity assay, HPLC, or other suitable tests.

The POI is preferably expressed employing conditions to produce yields of at least 1 mg/L, preferably at least 10 mg/L, preferably at least 100 mg/L, most preferred at least 1 g/L.

It is understood that the methods disclosed herein may further include cultivating said recombinant host cells under conditions permitting the expression of the POI, preferably in the secreted form or else as intracellular product. A recombinantly produced POI or a host cell metabolite can then be isolated from the cell culture medium and further purified by techniques well known to a person skilled in the art.

The POI produced according to the invention typically can be isolated and purified using state of the art techniques, including the increase of the concentration of the desired POI and/or the decrease of the concentration of at least one impurity.

If the POI is secreted from the cells, it can be isolated and purified from the culture medium using state of the art techniques. Secretion of the recombinant expression products from the host cells is generally advantageous for reasons that include facilitating the purification process, since the products are recovered from the culture supernatant rather than from the complex mixture of proteins that results when yeast cells are disrupted to release intracellular proteins.

The cultured transformant cells may also be ruptured sonically or mechanically, enzymatically or chemically to obtain a cell extract containing the desired POI, from which the POI is isolated and purified.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The highly purified product is essentially free from contaminating proteins, and preferably has a purity of at least 90%, more preferred at least 95%, or even at least 98%, up to 100%. The purified products may be obtained by purification of the cell culture supernatant or else from cellular debris.

As isolation and purification methods the following standard methods are preferred: Cell disruption (if the POI is obtained intracellularly), cell (debris) separation and wash by Microfiltration or Tangential Flow Filter (TFF) or centrifugation, POI purification by precipitation or heat treatment, POI activation by enzymatic digest, POI purification by chromatography, such as ion exchange (IEX), hydrophobic ointeraction chromatography (HIC), Affinity chromatography, size exclusion (SEC) or HPLC Chromatography, POI precipitation of concentration and washing by ultrafiltration steps.

The isolated and purified POI can be identified by conventional methods such as Western blot, HPLC, activity assay, or ELISA.

The POI can be any eukaryotic, prokaryotic or synthetic polypeptide. It can be a secreted protein or an intracellular protein. The present invention also provides for the recombinant production of functional homologs, functional equivalent variants, derivatives and biologically active fragments of naturally occurring proteins. Functional homologs are preferably identical with or correspond to and have the functional characteristics of a sequence.

A POI referred to herein may be a product homologous to the eukaryotic host cell or heterologous, preferably for therapeutic, prophylactic, diagnostic, analytic or industrial use.

The POI is preferably a heterologous recombinant polypeptide or protein, produced in a eukaryotic cell, preferably a yeast cell, preferably as secreted proteins. Examples of preferably produced proteins are immunoglobulins, immunoglobulin fragments, aprotinin, tissue factor pathway inhibitor or other protease inhibitors, and insulin or insulin precursors, insulin analogues, growth hormones, interleukins, tissue plasminogen activator, transforming growth factor a or b, glucagon, glucagon-like peptide 1 (GLP-1), glucagon-like peptide 2 (GLP-2), GRPP, Factor VII, Factor VIII, Factor XIII, platelet-derived growth factor1, serum albumin, enzymes, such as lipases or proteases, or a functional homolog, functional equivalent variant, derivative and biologically active fragment with a similar function as the native protein. The POI may be structurally similar to the native protein and may be derived from the native protein by addition of one or more amino acids to either or both the C- and N-terminal end or the side-chain of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

A POI can also be selected from substrates, enzymes, inhibitors or cofactors that provide for biochemical reactions in the host cell, with the aim to obtain the product of said biochemical reaction or a cascade of several reactions, e.g. to obtain a metabolite of the host cell. Exemplary products can be vitamins, such as riboflavin, organic acids, and alcohols, which can be obtained with increased yields following the expression of a recombinant protein or a POI according to the invention.

In general, the host cell, which expresses a recombinant product, can be any eukaryotic cell suitable for recombinant expression of a POI.

Examples of preferred mammalian cells are BHK, CHO (CHO-DG44, CHO-DUXB11, CHO-DUKX, CHO-K1, CHOK1SV, CHO-S), HeLa, HEK293, MDCK, NIH3T3, NS0, PER.C6, SP2/0 and VERO cells.

Examples of preferred yeast cells used as host cells according to the invention include but are not limited to the *Saccharomyces* genus (e.g. *Saccharomyces cerevisiae*), the *Pichia* genus (e.g. *P. pastoris*, or *P. methanolica*), the *Komagataella* genus (*K. pastoris, K. pseudopastoris* or *K. phaffii*), *Hansenula polymorpha* or *Kluyveromyces lactis*.

Newer literature divides and renames *Pichia pastoris* into *Komagataella pastoris, Komagataella phaffii* and *Komagataella pseudopastoris*. Herein *Pichia pastoris* is used synonymously for all, *Komagataella pastoris, Komagataella phaffii* and *Komagataella pseudo pastoris*.

The preferred yeast host cells are derived from methylotrophic yeast, such as from *Pichia* or *Komagataella*, e.g. *Pichia pastoris*, or *Komagataella pastoris*, or *K. phaffii*, or *K. pseudopastoris*. Examples of the host include yeasts such as *P. pastoris*. Examples of *P. pastoris* strains include CBS 704 (=NRRL Y-1603=DSMZ 70382), CBS 2612 (=NRRL Y-7556), CBS 7435 (=NRRL Y-11430), CBS 9173-9189 (CBS strains: CBS-KNAW Fungal Biodiversity Centre, Centraalbureau voor Schimmelcultures, Utrecht, The Netherlands), and DSMZ 70877 (German Collection of Microorganisms and Cell Cultures), but also strains from Invitrogen, such as X-33, GS115, KM71 and SMD1168. Examples of *S. cerevisiae* strains include W303, CEN.PK and the BY-series (EUROSCARF collection). All of the strains described above have been successfully used to produce transformants and express heterologous genes.

A preferred yeast host cell according to the invention, such as a *P. pastoris* or *S. cerevisiae* host cell, contains a heterologous or recombinant promoter sequences, which may be derived from a *P. pastoris* or *S. cerevisiae* strain, different from the production host. In another specific embodiment the host cell according to the invention comprises a recombinant expression construct according to the invention comprising the promoter originating from the same genus, species or strain as the host cell.

The promoter of the invention is preferably derived from a gene encoding a protein homologous to the host cell.

For example, a promoter according to the invention may be derived from yeast, such as a *S. cerevisiae* strain, and be used to express a POI in a yeast. A specifically preferred embodiment relates to a promoter according to the invention originating from *P. pastoris* for use in a method to produce a recombinant POI in a *P. pastoris* producer host cell line. The homologous origin of the nucleotide sequence facilitates its incorporation into the host cell of the same genus or species, thus enabling stable production of a POI, possibly with increased yields in industrial manufacturing processes. Also, functionally active variants of the promoter from other suitable yeasts or other fungi or from other organisms such as vertebrates or plants can be used.

If the POI is a protein homologous to the host cell, i.e. a protein which is naturally occurring in the host cell, the expression of the POI in the host cell may be modulated by the exchange of its native promoter sequence with a promoter sequence according to the invention.

This purpose may be achieved e.g. by transformation of a host cell with a recombinant DNA molecule comprising homologous sequences of the target gene to allow site specific recombination, the promoter sequence and a selective marker suitable for the host cell. The site specific recombination shall take place in order to operably link the promoter sequence with the nucleotide sequence encoding the POI. This results in the expression of the POI from the promoter sequence according to the invention instead of from the native promoter sequence.

In a specifically preferred embodiment of the invention the promoter sequence has an increased promoter activity relative to the native promoter sequence of the POI.

According to the invention it is preferred to provide a *P. pastoris* host cell line comprising a promoter sequence according to the invention operably linked to the nucleotide sequence coding for the POI.

According to the invention it is also possible to provide a wildcard vector or host cell according to the invention, which comprises a promoter according to the invention, and which is ready to incorporate a gene of interest encoding a POI. The wildcard cell line is, thus, a preformed host cell line, which is characterized for its expression capacity. This follows an innovative "wildcard" platform strategy for the generation of producer cell lines, for the POI production, e.g. using site-specific recombinase-mediated cassette exchange. Such a new host cell facilitates the cloning of a gene of interest (GOI), e.g. into predetermined genomic expression hot spots within days in order to get reproducible, highly efficient production cell lines.

According to a preferred embodiment the method according to the invention employs a recombinant nucleotide sequence encoding the POI, which is provided on a plasmid suitable for integration into the genome of the host cell, in a single copy or in multiple copies per cell. The recombinant nucleotide sequence encoding the POI may also be provided on an autonomously replicating plasmid in a single copy or in multiple copies per cell.

The preferred method according to the invention employs a plasmid, which is a eukaryotic expression vector, preferably a yeast expression vector. Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector, such as a yeast vector, which carries a DNA construct according to the invention. A preferred yeast expression vector is for expression in yeast selected from the group consisting of methylotrophic yeasts represented by the genera *Hansenula, Pichia, Candida* and *Torulopsis*.

In the present invention, it is preferred to use plasmids derived from pPICZ, pGAPZ, pPIC9, pPICZalfa, pGAPZalfa, pPIC9K, pGAPHis or pPUZZLE as the vector.

According to a preferred embodiment of the present invention, a recombinant construct is obtained by ligating the relevant genes into a vector. These genes can be stably integrated into the host cell genome by transforming the host cell using such vectors. The polypeptides encoded by the genes can be produced using the recombinant host cell line by culturing a transformant, thus obtained in an appropriate medium, isolating the expressed POI from the culture, and purifying it by a method appropriate for the expressed product, in particular to separate the POI from contaminating proteins.

Expression vectors may comprise one or more phenotypic selectable markers, e.g. a gene encoding a protein that confers antibiotic resistance or that supplies an autotrophic requirement. Yeast vectors commonly contain an origin of replication from a yeast plasmid, an autonomously replicating sequence (ARS), or alternatively, a sequence used for integration into the host genome, a promoter region, sequences for polyadenylation, sequences for transcription termination, and a selectable marker.

The procedures used to ligate the DNA sequences, e.g. coding for the precursing sequence and/or the POI, the promoter and the terminator, respectively, and to insert them into suitable vectors containing the information necessary for integration or host replication, are well known to persons skilled in the art, e.g. described by J. Sambrook et al., (A Laboratory Manual, Cold Spring Harbor, 1989).

It will be understood that the vector, which uses the regulatory elements according to the invention and/or the POI as an integration target, may be constructed either by first preparing a DNA construct containing the entire DNA sequence coding for the regulatory elements and/or the POI and subsequently inserting this fragment into a suitable expression vector, or by sequentially inserting DNA fragments containing genetic information for the individual elements, followed by ligation.

Also multicloning vectors, which are vectors having a multicloning site, can be used according to the invention, wherein a desired heterologous gene can be incorporated at a multicloning site to provide an expression vector. In expression vectors, the promoter is placed upstream of the gene of the POI and regulates the expression of the gene. In the case of multicloning vectors, because the gene of the POI is introduced at the multicloning site, the promoter is placed upstream of the multicloning site.

The DNA construct as provided to obtain a recombinant host cell according to the invention may be prepared synthetically by established standard methods, e.g. the phosphoramidite method. The DNA construct may also be of genomic or cDNA origin, for instance obtained by preparing a genomic or cDNA library and screening for DNA sequences coding for all or part of the polypeptide of the invention by hybridization using synthetic oligonucleotide probes in accordance with standard techniques (Sambrook et al., Molecular Cloning: A Laboratory Manual, Cold Spring Harbor, 1989). Finally, the DNA construct may be of mixed synthetic and genomic, mixed synthetic and cDNA or mixed genomic and cDNA origin prepared by annealing fragments of synthetic, genomic or cDNA origin, as appropriate, the fragments corresponding to various parts of the entire DNA construct, in accordance with standard techniques.

In another preferred embodiment, the yeast expression vector is able to stably integrate in the yeast genome, e.g. by homologous recombination.

A transformant host cell according to the invention obtained by transforming the cell with the regulatory elements according to the invention and/or the POI genes may preferably first be cultivated at conditions to grow efficiently to a large cell number. When the cell line is prepared for the POI expression, cultivation techniques are chosen to produce the expression product.

Specific examples relate to fed-batch fermentation of a recombinant production *P. pastoris* cell line producing reporter proteins, employing a glycerol batch medium and a glucose fed batch medium. Comparative promoter activity studies have proven that the promoter according to the invention may be successfully used for recombinant protein production.

According to a further example, human serum albumin (HSA) was produced as a POI under the glucose-limit conditions, and the HSA yield and gene copy number determined.

According to another example, fed-batch cultivation of *P. pastoris* strains expressing HSA under the control of a promoter according to the invention was performed.

Further examples refer to expressing a porcine carboxypeptidase B as model protein under transcriptional control of the pCS1 promoter.

Yet, a further example refers to the expression of an antibody fragment under the transcriptional control of pCS1.

A further example refers to size or length variants of a promoter according to the invention, such as the elongated pCS1 sequence pCS1a (SEQ ID NO:2) which comprises the pCS1 sequence and an elongation at the 5' end, or fragments of pCS1 with a length in the range of about 80 bp to 800 bp.

The foregoing description will be more fully understood with reference to the following examples. Such examples are, however, merely representative of methods of practicing one or more embodiments of the present invention and should not be read as limiting the scope of invention.

EXAMPLES

Examples below illustrate the materials and methods used to identify a new promoter and to analyze its expression properties in *Pichia pastoris*.

Example 1

Identification of a Strongly Expressed Gene in *P. Pastoris*

In order to identify a strong gene and its respective promoter of *P. pastoris*, analysis of gene expression patterns was done using DNA microarrays. *P. pastoris* cells grown in a glycerol batch and in glucose limit (chemostat) were analyzed.

a) Strain

A wild type *P. pastoris* strain (CBS2612, CBS-KNAW Fungal Biodiversity Centre, Centraalbureau voor Schimmelcultures, Utrecht, The Netherlands), which can grow on minimal media without supplements, was used.

b) Cultivation of *P. pastoris*

Fermentations were performed with Minifors reactors (Infors-HT, Switzerland) with a final working volume of 2.5 L.

Following media were used:

PTM$_1$ Trace Salts Stock Solution Contained Per Liter 6.0 g CuSO$_4$.5H$_2$O, 0.08 g NaI, 3.36 g MnSO$_4$.H$_2$O, 0.2 g Na$_2$MoO$_4$.2H$_2$O, 0.02 g H$_3$BO$_3$, 0.82 g CoCl$_2$, 20.0 g ZnCl$_2$, 65.0 g FeSO$_4$.7H$_2$O, 0.2 g biotin and 5.0 ml H$_2$SO$_4$ (95%-98%).

Glycerol Batch Medium Contained Per Liter 2 g Citric acid monohydrate (C$_6$H$_8$O$_7$.H$_2$O), 39.2 g Glycerol, 20.8 g NH$_4$H$_2$PO$_4$, 0.5 g MgSO$_4$.7H$_2$O, 1.6 g KCl, 0.022 g CaCl$_2$.2H$_2$O, 0.8 mg biotin and 4.6 ml PTM1 trace salts stock solution. HCl was added to set the pH to 5.

Glycerol Fed-Batch Medium Contained Per Liter 632 g glycerol, 8 g MgSO$_4$.7H$_2$O, 22 g KCl, and 0.058 g CaCl$_2$.2H$_2$O.

Chemostat Medium Contained Per Liter 2 g Citric acid monohydrate (C$_6$H$_8$O$_7$.H$_2$O), 99.42 g glucose monohydrate, 22 g NH$_4$H$_2$PO$_4$, 1.3 g MgSO$_4$.7H$_2$O, 3.4 g KCl, 0.02 g CaCl$_2$.2H$_2$O, 0.4 mg biotin and 3.2 ml PTM1 trace salts stock solution. HCl was added to set the pH to 5.

The dissolved oxygen was controlled at DO=20% with the stirrer speed (500-1250 rpm). Aeration rate was 60 L h$^{-1}$ air, the temperature was controlled at 25° C. and the pH setpoint of 5 was controlled with addition of NH$_4$OH (25%).

To start the fermentation, 1.5 L batch medium was sterile filtered into the fermenter and *P. pastoris* was inoculated (from an overnight pre-culture in YPG, 180 rpm, 28° C.) with a starting optical density (OD600) of 1. The batch phase of approximately 25 h reached a dry biomass concentration of approximately 20 g/L, it was followed by a 10 h exponential fed batch with glucose medium, leading to a dry biomass concentration of approximately 50 g/L. Then, the volume was reduced to 1.5 L and the chemostat cultivation was started with a feed/harvest rate of 0.15 L h$^{-1}$, resulting in a constant growth rate of μ=0.1. The fermentation was terminated 50 h after the chemostat start.

This fermentation has been performed three times to obtain the biological replicates necessary for reliable microarray analysis.

Carbon limited conditions (no detectable residual glucose) during the chemostat were verified by HPLC analysis of the culture supernatant.

c) Sampling

Samples were taken at the end of the glycerol batch phase and in steady state conditions of the glucose chemostat. Routine sampling as determination of optical density or yeast dry mass, qualitative microscopic inspection and cell viability analysis was done alongside during each fermentation. For microarray analysis, samples were taken and treated as follows: For optimal quenching, 9 mL cell culture broth was immediately mixed with 4.5 mL of ice cold 5% phenol (Sigma) solution (in Ethanol abs.), and aliquoted. Each 2 mL were centrifuged (13200 rpm for 1 minute) in pre-cooled collection tubes (GE healthcare, NJ), supernatant was removed completely and the tubes were stored at −80° C. until RNA purification.

d) RNA Purification and Sample Preparation for Microarray Hybridization

The RNA was isolated using TRI reagent according to the suppliers instructions (Ambion, US). The cell pellets were resuspended in TRI reagent and homogenized with glass beads using a FastPrep 24 (M.P. Biomedicals, CA) at 5 m s$^{-1}$ for 40 seconds. After addition of chloroform, the samples were centrifuged and the total RNA was precipitated from the aqueous phase by adding isopropanol. The pellet was washed with 70% ethanol, dried and re-suspended in RNAse free water. RNA concentrations were determined by measuring OD260 using a Nanodrop 1000 spectrophotometer (Nano-Drop products, DE). Remaining DNA from the samples was removed using the DNA free Kit (Ambion, CA). Sample volume equal to 10 μg RNA was diluted to 50 μL in RNAse free water, then DNAse buffer I and rDNAse I were added and incubated at 37° C. for 30 minutes. After addition of DNAse Inactivation Reagent, the sample was centrifuged and the supernatant was transferred into a fresh tube. RNA concentrations were determined again as described above. Additionally, RNA integrity was analyzed using RNA nano chips (Agilent). To monitor the microarray workflow from amplification and labelling to hybridisation of the samples, the Spike In Kit (Agilent, Product Nr.: 5188-5279) was used as positive control. It contains 10 different polyadenylated transcripts from an adenovirus, which are amplified, labelled and cohybridised together with the own RNA samples. The samples were labelled with Cy 3 and Cy 5 using the Quick Amp Labelling Kit (Agilent, Prod. Nr.: 5190-0444). Therefore 500 ng of purified sample RNA were diluted in 8.3 μL RNAse free water, 2 μL Spike A or B, and 1.2 μL T7 promoter primer were added. The mixture was denatured for 10 minutes at 65° C. and kept on ice for 5 minutes. Then 8.5 μL cDNA mastermix (per sample: 4 μL 5× first strand buffer, 2 μL 0.1 M DTT, 1 μL 10 mM dNTP mix, 1 μL MMLV-RT, 0.5 μL RNAse out) were added, incubated at 40° C. for 2 hours, then transferred to 65° C. for 15 minutes and put on ice for 5 minutes. The transcription mastermix (per sample: 15.3 μL nuclease free water, 20 μL transcription buffer, 6 μL 0.1 M DTT, 6.4 μL 50% PEG, 0.5 μL RNAse Inhibitor, 0.6 μL inorg. phosphatase, 0.8 μL T7 RNA Polymerase, 2.4 μL Cyanin 3 or Cyanin 5) was prepared and added to each tube and incubated at 40° C. for 2 hours. In order to purify the obtained labelled cRNA, the RNeasy Mini Kit (Qiagen, Cat. No. 74104) was used. Samples were stored at −80° C. Quantification of the cRNA concentration and labelling efficiency was done at the Nanodrop spectrophotometer.

e) Microarray Analysis

The Gene Expression Hybridisation Kit (Agilent, Cat. No. 5188-5242) was used for hybridisation of the labelled sample cRNAs. For the preparation of the hybridisation samples each 300 ng cRNA (Cy3 and Cy 5) and 6 μL 10-fold blocking agent were diluted with nuclease free water to a final volume of 24 μL. After addition of 1 μL 25-fold fragmentation buffer, the mixture was incubated at 60° C. for 30 minutes. Then 25 μL GEx Hybridisation Buffer HI-RPM was added to stop the reaction. After centrifugation for one minute with 13,200 rpm, the sample was chilled on ice and used for hybridisation immediately. In-house designed *P. pastoris* specific oligonucleotide arrays (AMAD-ID: 026594, 8×15K custom arrays, Agilent) were used. Microarray hybridisation was done according to the Microarray Hybridisation Chamber User Guide (Agilent G2534A). First, the gasket slide was uncovered and put onto the chamber base, Agilent label facing up. The sample (40 μL per array) was loaded in the middle of each of the eight squares. Then the microarray slide was carefully put onto the gasket slide (Agilent label facing down) and the chamber cover was placed on and fixed with the clamp. Hybridisation was done in the hybridisation oven for 17 hours at 65° C. Before scanning, the microarray chip was washed. Therefore, the chamber was dismantled, and the sandwich slides were detached from each other while submerged in wash buffer 1. The microarray was directly transferred into another dish with wash buffer 1, washed for 1 minute, transferred into wash buffer 2 (temperature at least 30° C.) and washed for another minute. After drying of the microarray slide by touching the slide edge with a tissue, it was put into the slide holder (Agilent label facing up). The slide holder was put into the carousel and scanning was started.

f) Data Acquisition and Statistical Evaluation of Microarray Data

Images were scanned at a resolution of 50 nm with a G2565AA Microarray scanner (Agilent) and were imported into the Agilent Feature Extraction 9.5 software. Agilent Feature Extraction 9.5 was used for the quantification of the spot intensities. The raw mean spot intensity data was then imported into the open source software R for further normalisation and data analysis.

For data preprocessing and normalization the R packages limma, vsn and marray were used. The intensity data was not background corrected and was normalized with VSN.

The microarray data was browsed for entries with high signal intensity in both states in order to identify strongly expressed constitutive genes. The most strongly transcribed gene is shown in Table 1, with the signal intensity in both states. The data of pGAP and pTEF are added as references. In average, pCS1 exceeded pGAP in both conditions (glycerol batch and glucose-limited chemostat cultivation) by roughly 30%, while pTEF is about 12% weaker than pGAP.

TABLE 1

Microarray data of the genes, which promoters were selected for further characterization and of pGAP and pTEF as controls

| Promoter | gene identifier | Intensity[1] | % of pGAP intensity/ transcription strength | Intensity[2] | % of pGAP intensity/ transcription strength |
|---|---|---|---|---|---|
| pGAP | PAS_chr2-1_0437 | 56235.2 | 100.0 | 44411.4 | 100.0 |
| pTEF | PAS_FragB_0052 | 47046.3 | 83.4 | 39956.2 | 89.9 |
| pCS1 | PAS_chr1-4_0586 | 83570.4 | 148.6 | 54723.2 | 122.7 |

[1] in glycerol batch phase (average of both channels)
[2] in glucose-limited chemostat (average of both channels)

Example 2

Comparative Promoter Activity Studies of the Newly Identified Promoter pCS1 in *P. pastoris* Using eGFP as Intracellularly Expressed Reporter Gene In order to analyze the properties of the newly identified promoter, shake flask screenings were performed as follows: Pre-culture for 24 hours was done with rich medium containing glycerol as carbon source—simulating the batch phase of the process, which was followed by the main culture with minimal medium and glucose feed beads—simulating the glucose-limited fed batch phase of the process.

a) Strain & Expression Vector

The *P. pastoris* wild type strain (CBS2612, CBS-KNAW Fungal Biodiversity Centre, Centraalbureau voor Schimmelcultures, Utrecht, The Netherlands) was used as host strain. Transformation of the strain was carried out with an in-house vector named pPUZZLE (Stadlmayr et al. J. Biotechnol 2010 December; 150(4):519-29), comprising of an origin of replication for *E. coli* (pUC19), an antibiotic resistance cassette (Sh ble gene conferring resistance to Zeocin) for selection in *E. coli* and yeast, an expression cassette for the gene of interest (GOI) consisting of a multiple cloning site and the *S. cerevisiae* CYC1 transcription terminator, and a locus for integration into the *P. pastoris* genome (3'AOX1 region).

b) Amplification and Cloning of the Newly Identified Promoter pCS1 into pPUZZLE Expression Vector Containing eGFP as GOI The pCS1 promoter comprises 985 bp of the 5'-non coding region of the CS1 gene (see Example 1) up to the start codon ATG and was amplified by PCR (Phusion Polymerase, New England Biolabs) from *P. pastoris* genomic DNA using the primers shown in Table 2. The sequence was cloned into the pPUZZLE expression vector pPM1aZ10_eGFP, resulting in pPM1aZ10_pCS1_eGFP. Additionally, the vector pPM1aZ10_pGAP_eGFP, containing the commonly used promoter of glyceraldehyde 3-phosphate dehydrogenase promoter (pGAP of *P. pastoris*, here SEQ ID NO:13) was used as reference. The promoters were inserted upstream of the start codon of the eGFP gene using the ApaI and the SbfI restriction sites (see Tables 2 and 3). The correctness of the promoter sequences was verified by Sanger sequencing.

TABLE 2

Primers for PCR amplification of the promoters

| Name | Target | Sequence | $T_M$ | Restriction site |
|---|---|---|---|---|
| pCS1_fw | pCS1 | SEQ ID NO: 14 GATAGGGCCCCAGGGCAT CATTGAGGTTTCCAC | 69.6 | ApaI |
| pCS1_back | pCS1 | SEQ ID NO: 15 GATACCTGCAGGTTTTGT TGTTGAGTGAAGCGAGTG | 69.3 | SbfI |

TABLE 3

Amplification primers, cloning enzymes and the length of the cloned promoter

| promoter | 5'primer | 3'primer | Cloning enzyme 5' | Cloning enzyme 3' | length |
|---|---|---|---|---|---|
| pCS1 | pCS1_fw | pCS1_back | ApaI | SbfI | 985 | c) Expression of eGFP in *P. pastoris* for Analysis of the Promoter Activity

All plasmids were linearized with AscI within the 3'AOX genome integration region prior to electroporation (2 kV, 4 ms, GenePulser, BioRad) into electrocompetent *P. pastoris*.

Positive transformants were selected on YPD plates (per liter: 10 g yeast extract, 20 g peptone, 20 g glucose, 20 g agar-agar) plates containing 25 μg/mL of Zeocin (Invivogen, CA). Colony PCR was used to ensure the presence of the transformed plasmid. Therefore, genomic DNA was gained by cooking and freezing of *P. pastoris* colonies for 5 minutes each and directly applied for PCR with the appropriate primers. For expression screening, a single colony was inoculated in liquid YPG-Zeo medium (per liter: 20 g peptone, 10 g yeast extract, 12.6 g glycerol and 25 mg Zeocin) as pre-culture. After approximately 24 h the pre-culture was used to inoculate the main culture with an OD600 of 0.1 in 2 ml YP medium (per liter: 20 g peptone, 10 g yeast extract) and 2 glucose feed bead quarters (Kuhner, CH). Glucose-limiting growth conditions were achieved due to the slow glucose release kinetics of these feed beads, which is described by the following equation: (Glucose)=1.63*t0.74 [mg/Disc]. Samples were taken at the end of the pre-culture, and 24 and 48 hours after inoculation of the main culture. Cell density was determined by measuring OD600, eGFP expression was analyzed by flow cytometry as described in Stadlmayr et al. (J. Biotechnology 2010 December; 150(4):519-29). For each sample 10,000 cells were analyzed. Auto-fluorescence of P. pastoris was measured using untransformed P. pastoris wild type cells and subtracted from the signal. Relative eGFP expression levels (fluorescence intensity related to cell size) are shown as percentage of eGFP expression level of a clone expressing eGFP under the control of the constitutive pGAP promoter.

The results are shown in Table 4. The clone expressing under the control of the pCS1 promoter exceeded pGAP by 38% at the pre-culture (batch) end, and had 4-fold higher GFP expression levels at the main culture (fed batch) end.

TABLE 4

Average GFP fluorescence per cell size of P. pastoris clones expressing eGFP under the control of the novel pCS1 promoter. Data is shown relative to pGAP at the same time point.

|  | pre-culture | | main culture | |
| --- | --- | --- | --- | --- |
|  | batch end | stdev | 48 h | stdev |
| pCS1 | 138.2 | 26.6 | 400.7 | 104.87 |
| pGAP | 100.0 | | 100.0 | | d) Analysis of pCS1 Promoter Strength in Fed-Batch Fermentation of One eGFP Clone Fed batch fermentations were performed in DASGIP reactors with a final working volume of 1.0 L.

Following media were used:

PTM$_1$ Trace Salts Stock Solution Contained Per Liter 6.0 g CuSO$_4$.5H$_2$O, 0.08 g NaI, 3.36 g MnSO$_4$.H$_2$O, 0.2 g Na$_2$MoO$_4$.2H$_2$O, 0.02 g H$_3$BO$_3$, 0.82 g CoCl$_2$, 20.0 g ZnCl$_2$, 65.0 g FeSO$_4$.7H$_2$O, 0.2 g biotin and 5.0 ml H$_2$SO$_4$ (95%-98%).

Glycerol Batch Medium Contained Per Liter 2 g Citric acid monohydrate (C$_6$H$_8$O$_7$.H$_2$O), 39.2 g Glycerol, 12.6 g NH$_4$H$_2$PO$_4$, 0.5 g MgSO$_4$.7H$_2$O, 0.9 g KCl, 0.022 g CaCl$_2$.2H$_2$O, 0.4 mg biotin and 4.6 ml PTM1 trace salts stock solution. HCl was added to set the pH to 5.

Glucose Fed Batch Medium Contained Per Liter 464 g glucose monohydrate, 5.2 g MgSO$_4$.7H$_2$O, 8.4 g KCl, 0.28 g CaCl$_2$.2H$_2$O, 0.34 mg biotin and 10.1 mL PTM1 trace salts stock solution.

The dissolved oxygen was controlled at DO=20% with the stirrer speed (400-1200 rpm). Aeration rate was 24 L h$^{-1}$ air, the temperature was controlled at 25° C. and the pH setpoint of 5 was controlled with addition of NH$_4$OH (25%).

To start the fermentation, 400 mL batch medium was sterile filtered into the fermenter and P. pastoris clone pCS1_eGFP#1 was inoculated (from pre-culture) with a starting optical density (OD600) of 1. The batch phase of approximately 25 h (reaching a dry biomass concentration of approximately 20 g/L) was followed by a glucose-limited fed batch starting with an exponential feed for 7 h and a constant feed rate of 15 g/L for 13 h, leading to a final dry biomass concentration of approximately 110 g/L. Samples were taken during batch and fed batch phase, and analyzed for eGFP expression using a plate reader (Infinite 200, Tecan, CH). Therefore, samples were diluted to an optical density (OD600) of 5. Fermentations were performed in duplicates. Results are shown in Table 5 as relative fluorescence per bioreactor (FL/r). The clone expressing under control of the pCS1 promoter had on average 4.2 fold higher eGFP expression compared to pGAP during the whole fermentation process.

TABLE 5

Relative fluorescence per bioreactor of two different P. pastoris clones expressing eGFP under the control of pGAP or pCS1 in an optimized fed batch fermentation. t indicates feed time, µ indicates mean specific growth rate of all four cultivations.

|  | pGAP_eGFP#2 | | pCS1_eGFP#1 | | comparison FL/r pCS1/ | Growth rate |
| --- | --- | --- | --- | --- | --- | --- |
| t [h] | FL/r | STDEV | FL/r | STDEV | pGAP | µ [h$^{-1}$] |
| −4.5 | 2.1 | 0.1 | 9.3 | 0.6 | 4.4 | µ +/− Std. Dev. |
| 0.8 | 4.7 | 0.1 | 16.8 | 0.9 | 3.6 | 0.123 +/− 0.015 |
| 2.3 | 5.9 | 1 | 20.2 | 1.5 | 3.4 | 0.134 +/− 0.013 |
| 4.3 | 9.2 | 0.1 | 35.3 | 1.4 | 3.8 | 0.127 +/− 0.009 |
| 6.8 | 14.2 | 0.6 | 57.6 | 4 | 4.1 | 0.114 +/− 0.004 |
| 17.9 | 57.6 | 4.2 | 288.2 | 15.6 | 5 | 0.055 +/− 0.006 |
| 19.9 | 86 | 16.6 | 337.3 | 26.5 | 3.9 | 0.064 +/− 0.020 |
| 21.6 | 73.9 | 9.7 | 379.9 | 41.7 | 5.1 | 0.018 +/− 0.004 |

Example 3

Comparative Promoter Activity Studies of the Newly Identified Promoter pCS1 in P. pastoris Using Human Serum Albumin (HSA) as Extracellular Expressed Reporter Gene In order to analyze the properties of the newly identified promoter under glucose limit conditions, shake flask screenings were performed as follows: Pre-culture for 24 hours was done in rich medium containing glycerol as carbon source—simulating the batch phase of the process, which was followed by the main culture in buffered rich medium (2% glucose). The main culture was fed with 0.5% glucose every 12 hours.

a) Strain & Expression Vector

The P. pastoris wild type strain (CBS2612, CBS-KNAW Fungal Biodiversity Centre, Centraalbureau voor Schimmelcultures, Utrecht, The Netherlands) was used as host strain. Transformation of the strain was carried out with an in-house vector named pPUZZLE (Stadlmayr et al. J. Biotechnol 2010 December; 150(4):519-29), selection of positive transformants was based on the Zeocin resistance. For secretory expression of human serum albumin (HSA) its native secretion leader was used.

b) Amplification and Cloning of the Newly Identified Promoter pCS1 into an in-House Expression Vector The promoter amplified in Example 2b was cloned into the pPUZZLE expression vector pPM1aZ10_HSA, resulting in pPM1aZ10_pCS1_HSA. Additionally, the vector pPM1aZ10_pGAP_HSA, containing the commonly used promoter of glyceraldehyde 3-phosphate dehydrogenase promoter (pGAP) was used as reference. The promoters were inserted upstream of the start codon of the HSA gene using the ApaI and the SbfI restriction sites (see Table 3). The correctness of the promoter sequences was verified by Sanger sequencing.

c) Expression of HSA in P. pastoris Under Control of the Newly Identified Promoter pCS1

All plasmids were linearized using AscI restriction enzyme prior to electroporation (using a standard transformation protocol for P. pastoris) into P. pastoris. Selection of positive transformants was performed on YPD plates (per liter: 10 g yeast extract, 20 g peptone, 20 g glucose, 20 g agar-agar) plates containing 25 µg/mL of Zeocin. Colony PCR was used to ensure the presence of the transformed plasmid as described in Example 2c.

For HSA expression screening, a single colony was inoculated in liquid YPG-Zeo medium (per liter: 20 g peptone, 10 g yeast extract, 12.6 g glycerol and 25 mg Zeocin) as pre-culture. After approximately 24 h the pre-culture was used to inoculate the main culture with an OD600 of 1 in YPD medium (per liter: 20 g peptone, 10 g yeast extract, 20 g glucose). The main culture was fed with 0.5% glucose every 12 hours. Samples were taken at the end of the pre-culture, and 24 and 48 hours after inoculation of the main culture. Biomass concentration was determined by measuring OD600 or wet cell weight. HSA concentration in the culture supernatant was quantified by the Human Albumin ELISA Quantitation Set (Cat. No. E80-129, Bethyl Laboratories, TX, USA) following the supplier's instruction manual. The HSA standard was used with a starting concentration of 400 ng $mL^{-1}$. Samples were diluted accordingly in sample diluent (50 mM Tris-HCl, 140 mM NaCl, 1% (w/v) BSA, 0.05% (v/v) Tween20, pH 8.0). HSA titers from screening of clones expressing HSA under the control of pGAP (1 HSA gene copy) and of 9 clones expressing eGFP under the control of pCS1 are presented in Table 6. All pCS1-controlled clones secrete twice the amount of HSA as the pGAP-controlled clone with one gene copy.

TABLE 6

Quantification of secreted HSA levels in supernatants of *P. pastoris* clones expressing HSA under the control of pGAP and pCS1.

| clone | HSA [mg/L] 48 h main culture |
|---|---|
| pGAP_HSA #3 (1GCN) | 32.8 |
| pCS1_HSA | 76.5 +/− 5.0 |

Example 4

Fed-Batch Cultivation of *P. Pastoris* Strains Expressing HSA Under Control of the pCS1 Promoter The fermentations were performed in DASGIP bioreactors with a final working volume of 1.0 L. Two different *P. pastoris* strains expressing HSA under control of pGAP (pGAP_HSA#3 having one HSA gene copy, and pGAP_HSA#4 having two HSA gene copies) were cultivated as reference.

Following media were used:
PTM$_1$ Trace Salts Stock Solution Contained Per Liter
6.0 g CuSO$_4$.5H$_2$O, 0.08 g NaI, 3.36 g MnSO$_4$.H$_2$O, 0.2 g Na$_2$MoO$_4$.2H$_2$O, 0.02 g H$_3$BO$_3$, 0.82 g CoCl$_2$, 20.0 g ZnCl$_2$, 65.0 g FeSO$_4$.7H$_2$O, 0.2 g biotin and 5.0 ml H$_2$SO$_4$ (95%-98%).

Glycerol Batch Medium Contained Per Liter
39.2 g Glycerol, 27.9 g H$_3$PO$_4$ (85%), 7.8 g MgSO$_4$.7H$_2$O, 2.6 g KOH, 9.5 g K$_2$SO$_4$, 0.6 g CaSO$_4$.2H$_2$O, 0.4 mg biotin and 4.6 ml PTM1 trace salts stock solution. The pH was adjusted to 5.85 after sterile filtering into the fermenter.

Glucose Fed Batch Medium Contained Per Liter
550 g glucose monohydrate, 6.5 g MgSO$_4$.7H$_2$O, 10 g KCl, 0.35 g CaCl$_2$.2H$_2$O, 0.4 mg biotin and 12 ml PTM1 trace salts stock solution.

The dissolved oxygen was controlled at DO=20% with the stirrer speed (400-1200 rpm). Aeration rate is 24 l h$^{-1}$ air, the temperature was controlled at 25° C. and the pH setpoint of 5.85 is controlled with addition of NH$_4$OH (25%).

To start the fermentation, 400 ml batch medium was sterile filtered into the fermenter and *P. pastoris* was inoculated (from pre-culture) with a starting optical density (OD600) of 1. The batch phase of approximately 25 h reached a dry biomass concentration of approximately 20 g/L and was followed by a constant fed batch (for 100 hours) with glucose medium, leading to a dry biomass concentration of approximately 100 g/L. The pH was 5.85 during batch, and kept at 5.85 throughout the fermentation. Samples were taken during batch and fed batch phase. HSA concentration was quantified using the Human Albumin ELISA Quantitation Set (Bethyl, Cat. No. E80-129) as described in Example 3c.

Two clones secreting HSA under control of pCS1 reached at least 2-fold higher HSA titers at the end of batch and fed batch compared to a single copy pGAP clone.

Example 5

Determination of Gene Copy Numbers (GCN) of Selected Clones

Expression strength is often correlated to the number of expression cassettes integrated into the *P. pastoris* genome. Therefore the gene copy number of selected clones is determined. Genomic DNA is isolated using the DNeasy Blood&Tissue Kit (Quiagen, Cat. No. 69504). Gene copy numbers are determined using quantitative PCR. Therefore, SensiMix SYBR Kit (Bioline, QT605-05) is used. The Sensi Mix SYBR is mixed with the primers and the sample and applied for real time analysis in a real-time PCR cycler (Rotor Gene, Qiagen). All samples are analyzed in tri- or quadruplicates. Rotor Gene software is used for data analysis.

Example 6

Comparative Promoter Activity Studies of the Newly Identified Promoter pCS1 in *P. pastoris* Using Porcine Carboxypeptidase B (CpB) as Extracellular Expressed Reporter Gene In order to analyze the properties of the newly identified promoter, shake flask screenings are performed as follows: Pre-culture for 24 hours is done with rich medium containing glycerol as carbon source, which is followed by the main culture with rich media.

a) Strain & Expression Vector

The *P. pastoris* wild type strain (CBS2612, CBS-KNAW Fungal Biodiversity Centre, Centraalbureau voor Schimmelcultures, Utrecht, The Netherlands) is used as host strain. Transformation of the strain is carried out with an in-house vector named pPUZZLE (Stadlmayr et al. J. Biotechnol 2010 December; 150(4):519-29), selection of positive transformants is based on the Zeocin resistance. For secretory expression of porcine carboxypeptidase B (CpB) yeast alpha mating factor leader is used.

b) Amplification and Cloning of the Newly Identified Promoter pCS1 into an In-House Expression Vector The promoter amplified in Example 2b are cloned into the pPUZZLE expression vector pPM1aZ30_aMF_CpB, resulting in pPM1aZ30_pCS1_aMF_CpB. Additionally, the vector pPM1dZ30_pGAP_CpB, containing the commonly used promoter of glyceraldehyde 3-phosphate dehydrogenase promoter (pGAP) is used as reference. The promoters are inserted upstream of the start codon of the CpB gene using the ApaI and the SbfI restriction sites The correctness of the promoter sequences is verified by Sanger sequencing.

c) Expression of CpB in *P. pastoris* Under Control of the Newly Identified Glucose-Limit Induced Promoters Plasmids are linearized using AscI restriction enzyme prior to electroporation (using a standard transformation protocol for *P. pastoris*) into *P. pastoris*. Selection of positive transformants is performed on YPD plates (per liter: 10 g yeast extract, 20 g peptone, 20 g glucose, 20 g agar-agar) plates containing 25 µg/mL of Zeocin. Colony PCR is used to ensure the presence of the transformed plasmid as described in Example 2c.

For CpB expression screening, a single colony is inoculated in liquid YPG-Zeo medium (per liter: 20 g peptone, 10 g yeast extract, 12.6 g glycerol and 25 mg Zeocin) as pre-culture. After approximately 24 h the pre-culture is used to inoculate the main culture with an OD600 of 1 in YPD medium (per liter: 20 g peptone, 10 g yeast extract, 20 g glucose). Main culture is fed with 0.5% glucose every 12 hours. Samples are taken at the end of the pre-culture, and 24 and 48 hours after inoculation of the main culture. Biomass concentration is determined by measuring OD600 or wet cell weight. CpB concentration in the culture supernatant is quantified by an enzymatic assay, based on the conversion of hippuryl-L-arginine to hippuric acid by the CpB. Reaction kinetics are measured by monitoring the absorption at 254 nm at 25° C. using a Hitachi U-2910 Spectrophotometer when the reaction is started. Samples and standards are buffered with assay buffer (25 mM Tris, 100 mM HCl, pH 7.65) and are activated using activation buffer (0.01 mgL-1 Trypsin, 300 mM Tris, 1 µM $ZnCl_2$, pH 7.65). Activation buffer without trypsin is used instead of sample as negative control. The reaction is started by adding the substrate solution (1 mM hippuryl-L-arginine in assay buffer).

d) Fed-Batch Cultivation of *P. pastoris* Strains Expressing CpB Under Control of the pCS1 Promoter Fed Batch Fermentation is Done as Described in Example 4 Using Media as Described in Example 2d Example 7

Comparative Promoter Activity Studies of the Newly Identified Promoter pCS1 in *P. pastoris* Multicopy Clones Using Human Serum Albumin (HSA) as Extracellular Expressed Reporter Gene In order to analyze the properties of the newly identified promoter pCS1, shake flask screenings are performed as follows: Pre-culture for 24 hours is done with rich medium containing glycerol as carbon source, which is followed by the main culture with rich medium.

a) Strain & Expression Vector

The *P. pastoris* wild type strain (CBS2612, CBS-KNAW Fungal Biodiversity Centre, Centraalbureau voor Schimmelcultures, Utrecht, The Netherlands) is used as host strain. Transformation of the strain is carried out with an in-house vector named pPUZZLE (Stadlmayr et al. J. Biotechnol 2010 December; 150(4):519-29), selection of positive transformants is based on the Zeocin resistance. For secretory expression of human serum albumin (HSA) its native secretion leader is used.

b) Amplification and Cloning of the Newly Identified Promoter pCS1 into an in-House Expression Vector The promoter amplified in Example 2b is cloned into the pPUZZLE expression vector pPM1nZ30_HSA, resulting in pPM1nZ30_pCS1_HSA.

The promoter is inserted upstream of the start codon of the HSA gene using the ApaI and the SbfI restriction sites. The correctness of the promoter sequences is verified by Sanger sequencing.

c) Expression of HSA in *P. pastoris* Under Control of the Newly Identified Promoter pCS1

Plasmids are linearized using AscI restriction enzyme prior to electroporation (using a standard transformation protocol for *P. pastoris*) into *P. pastoris*. Selection of positive transformants is performed on YPD plates (per liter: 10 g yeast extract, 20 g peptone, 20 g glucose, 20 g agar-agar) plates containing 25 µg/mL of Zeocin. Gene copy number amplification is done as described in Marx et al. (FEMS Yeast Res. 2009 December; 9(8):1260-70). Colony PCR is used to ensure the presence of the transformed plasmid as described in Example 2c.

For HSA expression screening, a single colony is inoculated in liquid YPG-Zeo medium (per liter: 20 g peptone, 10 g yeast extract, 12.6 g glycerol and 25 mg Zeocin) as pre-culture. After approximately 24 h the pre-culture is used to inoculate the main culture with an OD600 of 1 in YPD medium (per liter: 20 g peptone, 10 g yeast extract, 20 g glucose). The main culture is fed with 0.5% glucose every 12 hours. Samples are taken at the end of the pre-culture, and 24 and 48 hours after inoculation of the main culture. Biomass concentration is determined by measuring OD600 or wet cell weight. HSA concentration in the culture supernatant is quantified by the Human Albumin ELISA Quantitation Set (Cat. No. E80-129, Bethyl Laboratories, TX, USA) following the supplier's instruction manual. The HSA standard is used with a starting concentration of 400 ng $mL^{-1}$. Samples were diluted accordingly in sample diluent (50 mM Tris-HCl, 140 mM NaCl, 1% (w/v) BSA, 0.05% (v/v) Tween20, pH 8.0).

Example 8

Comparative Promoter Activity Studies of the Newly Identified Promoter pCS1 in *P. pastoris* Using Antibody Fragment (Fab) as Extracellular Expressed Reporter Gene In order to analyze the properties of the newly identified promoter, shake flask screenings are performed as follows: Pre-culture for 24 hours is done with rich medium containing glycerol as carbon source, which is followed by the main culture with rich medium.

a) Strain & Expression Vector

The *P. pastoris* wild type strain (CBS2612, CBS-KNAW Fungal Biodiversity Centre, Centraalbureau voor Schimmelcultures, Utrecht, The Netherlands) is used as host strain. Transformation of the strain is carried out with an in-house vector named pPUZZLE (Stadlmayr et al. J. Biotechnol 2010 December; 150(4):519-29), selection of positive transformants is based on the Zeocin resistance. For secretory expression of an antibody Fab fragment, yeast alpha mating factor leader is used.

b) Amplification and Cloning of the Newly Identified Promoter pCS1 into an in-House Expression Vector The pCS1 promoter amplified in Example 2b is cloned into the pPUZZLE expression vector containing Fab as GOI. The promoter is inserted upstream of the start codon of the Fab gene using the ApaI and the SbfI restriction sites. The correctness of the promoter sequence is verified by Sanger sequencing.

c) Expression of Fab in *P. pastoris* Under Control of the Newly Identified Promoter pCS1

Plasmids are linearized using AscI restriction enzyme prior to electroporation (using a standard transformation protocol for *P. pastoris*) into *P. pastoris*. Selection of positive transformants is performed on YPD plates (per liter: 10 g yeast extract, 20 g peptone, 20 g glucose, 20 g agar-agar) plates containing 25 µg/mL of Zeocin. Colony PCR is used to ensure the presence of the transformed plasmid as described in Example 2c.

For Fab expression screening, a single colony is inoculated in liquid YPG-Zeo medium (per liter: 20 g peptone, 10 g yeast extract, 12.6 g glycerol and 25 mg Zeocin) as pre-culture. After approximately 24 h the pre-culture is used to inoculate the main culture with an OD600 of 1 in YPD medium (per liter: 20 g peptone, 10 g yeast extract, 20 g glucose). The main culture is fed with 0.5% glucose every 12 hours. Samples are taken at the end of the pre-culture, and 24 and 48 hours after inoculation of the main culture. Biomass concentration is determined by measuring OD600 or wet cell weight. Quantification of intact Fab is done by ELISA using anti-human IgG antibody (Abcam ab7497) as coating antibody (1:1,000), and a goat anti-Human Kappa Light Chains (Bound and Free)-alkaline phosphatase conjugated antibody (Sigma A3813) as detection antibody (1:1,000). Human Fab/Kappa, IgG fragment (Bethyl P80-115) is used as standard with a starting concentration of 50 ng/mL. Supernatant samples are diluted accordingly. Detection is done with pNPP substrate (Sigma S0942). Coating-, Dilution- and Washing buffer were based on PBS (2 mM $KH_2PO_4$, 10 mM $Na_2HPO_4.2H_2O$, 2.7 mM g KCl, 8 mM NaCl, pH 7.4) and completed with BSA (1% (w/v)) and/or Tween20 (0.1% (v/v)) accordingly.

d) Fed-batch cultivation of *P. pastoris* strains expressing Fab under control of the pCS1 promoter. Fed batch fermentations are done similar as described in example 4 using media as described in example 2d.

Example 9

Comparison of Variants of pCS1

Length variants of the pCS1 promoter are cloned as described in example 2a and screened similar as described in example 2c. Clones expressing under the control of pCS1 (standard length) and pGAP are used as controls. Forward primers and lengths of pCS1 and its variants are listed in Table 7.

TABLE 7 pCS1 and its variants: forward primers and lengths of the pCS1 size variants (SEQ ID NO: 1)

| variants | forward primer | Length (bp) |
|---|---|---|
| pCS1 (standard) SEQ ID NO: 1 | GATAGGGCCCCAGGGCATCATT GAGGTTTCCAC SEQ ID NO: 16 | 985 |
| pCS1-1488 SEQ ID NO: 2 | GATAGGGCCCGATAGTTCTAGAAG ACCTGGCGTCG SEQ ID NO: 17 | 1488 |
| pCS1-767F SEQ ID NO: 3 | GATAGGGCCCAGCCAACCATCT TTTGTTTCG SEQ ID NO: 18 | 767 |
| pCS1-500F SEQ ID NO: 4 | GATAGGGCCCGTGGTTTCCAGG ACAACACCC SEQ ID NO: 19 | 500 |
| pCS1-344F SEQ ID NO: 5 | GATAGGGCCCGACCGCAATTCA CCATGATGC SEQ ID NO: 20 | 344 |

TABLE 7 -continued pCS1 and its variants: forward primers and lengths of the pCS1 size variants (SEQ ID NO: 1)

| variants | forward primer | Length (bp) |
|---|---|---|
| pCS1-234F SEQ ID NO: 6 | GATAGGGCCCAGCCTGCTTCAT TCCTGCC SEQ ID NO: 21 | 234 |
| pCS1-138F SEQ ID NO: 7 | GATAGGGCCCCCGCGAAAAAGG TTTGTTTATAG SEQ ID NO: 22 | 138 |
| pCS1-85F SEQ ID NO: 8 | GATAGGGCCCCATACTCTCCTC CCCCCCTG SEQ ID NO: 23 | 85 |

Example 10

Verification of Expression Strength of a Promoter in a Clone Expressing eGFP Under Control of Said Promoter in Growth-Limited Conditions at High and Low Growth Rates a) Strain A host strain (e.g. *Pichia pastoris*) expressing eGFP under control of a "promoter of interest" and a strain expressing eGFP under control of pGAP are used to compare expression levels.

b) Cultivation of eGFP Expressing Strains for Promoter Comparison

These strains are cultivated in chemostat at two fixed specific growth rates (one low, one high specific growth rate by setting the dilution rate), using DASGIP bioreactors with a final working volume of 1.0 L.

Following media are used:

PTM1 trace salts stock solution contains per liter
6.0 g $CuSO_4.5H_2O$, 0.08 g NaI, 3.36 g $MnSO_4.H_2O$, 0.2 g $Na_2MoO_4.2H_2O$, 0.02 g $H_3BO_3$, 0.82 g $CoCl_2$, 20.0 g $ZnCl_2$, 65.0 g $FeSO_4.7H_2O$, 0.2 g biotin and 5.0 ml $H_2SO_4$ (95%-98%).

Glycerol Batch Medium Contains Per Liter
2 g Citric acid monohydrate ($C_6H_8O_7.H_2O$), 39.2 g Glycerol, 12.6 g $NH_4H_2PO_4$, 0.5 g $MgSO_4.7H_2O$, 0.9 g KCl, 0.022 g $CaCl_2.2H_2O$, 0.4 mg biotin and 4.6 ml PTM1 trace salts stock solution. HCl is added to set the pH to 5.

Chemostat Medium Contains Per Liter
2.5 g Citric acid monohydrate ($C_6H_8O_7.H_2O$), 55.0 g glucose monohydrate, 21.75 g $(NH_4)_2HPO_4$, 1.0 g $MgSO_4.7H_2O$, 2.5 g KCl, 0.04 g $CaCl_2.2H_2O$, 0.4 mg biotin and 2.43 mL PTM1 trace salts stock solution. HCl is added to set the pH to 5.

The dissolved oxygen is controlled at DO=20% with the stirrer speed (400-1200 rpm). Aeration rate is 24 L $h^{-1}$ air, the temperature is controlled at 25° C. and the pH setpoint of 5 is controlled with addition of $NH_4OH$ (25%).

To start the fermentation, 400 mL batch medium is sterile filtered into the fermenter and a *P. pastoris* clone is inoculated (from pre-culture) with a starting optical density (OD600) of 1. The batch phase of approximately 25 h (reaching a dry biomass concentration of approximately 20 g $L^{-1}$) is followed by glucose-limited chemostat cultivation. The feed rate of chemostat medium and the harvest rate are used to keep a constant specific growth rate as desired. During this cultivation, culture broth volume is kept constant and cell dry weight is determined in order to ensure a constant growth rate. Cells are cultivated at a high and low growth rate of 0.15 and 0.015 h⁻¹, respectively. Therefore, the feed/harvest rate is controlled at 150 mL h⁻¹ L⁻¹ (mL chemostat medium per liter culture broth and hour) and 15 mL h⁻¹ L⁻¹, respectively.

c) Sampling

Samples are taken in steady state conditions (after at least 5 volume exchanges) and analyzed for eGFP expression using a plate reader (Infinite 200, Tecan, CH). Therefore, samples are diluted to an optical density (OD600) of 5. Fermentations are performed in duplicates. Expression data is compared by calculating relative fluorescence per bioreactor as described in example 2d).

Example 11

Identification of a *P. pastoris* Promoter Enabling High Transcription at High and Low Specific Growth Rates In order to identify a promoter enabling high transcription at high and low growth rates, analysis of gene expression patterns is done using DNA microarrays. Genes displaying high transcription strength at high and low growth rates are selected from the transcriptomics data.

Therefore, *P. pastoris* cells are grown in chemostat cultivation as described in example 10b) at high and low specific growth rates of 0.15 and 0.015 h⁻¹, respectively. Sampling, RNA purification, sample preparation for microarray hybridization, microarray analysis, data acquisition and statistical evaluation are done as described in example 1c), 1d), 1e) and 1f).

Genes and respective promoters with high transcription strength at high and low growth rate are identified by browsing the microarray data for genes with high signal intensities in both, high and low growth rate conditions. As a second criterion, signal intensities should be higher as those of the glyceraldehyde-3-phosphate dehydrogenase (GAP, synonyms GAPDH and TDH3) gene in both conditions. To isolate the promoter, a nucleic acid fragment of approximately 1000 bps upstream of the start codon ATG of the respective gene is amplified.

The invention claimed is:

1. An isolated nucleic acid sequence comprising SEQ ID NO:1, a variant having at least 90% homology to SEQ ID NO:1, operably linked to a heterologous nucleotide sequence encoding a protein of interest (POI).

2. The nucleic acid sequence according to claim 1, comprising at least one further sequence selected from the group consisting of SEQ ID NO:1, variants having at least 90% homology to SEQ ID NO:1, or fragments thereof from 80 to 1500 bp in length.

3. The nucleic acid sequence according to claim 2, wherein the size variant of SEQ ID NO:1 comprises the nucleic acid sequence selected from the group consisting of SEQ ID NOs: 2, 3, 4, 5, 6, 7 and 8.

4. The nucleic acid sequence according to claim 1, wherein the variant is a homolog obtainable by modifying the nucleotide sequence of SEQ ID NO:1 or size variants thereof, by insertion, deletion or substitution of one or more nucleotides within the sequence or at either or both of the distal ends of the sequence.

5. The nucleic acid sequence according to claim 4, wherein the homologs are obtainable by modifying the nucleotide sequence of SEQ ID NO:1 or size variants thereof, by insertion, deletion or substitution of one or more nucleotides within the sequence or at either or both of the distal ends of the sequence with a nucleotide sequence of 80 bp to 1500 bp.

6. The nucleic acid sequence according to claim 4, wherein the homologs are obtainable by modifying the nucleotide sequence of SEQ ID NO:1 or size variants thereof, by insertion, deletion or substitution of one or more nucleotides within the sequence or at either or both of the distal ends of the sequence with a nucleotide sequence of at least 200 bp.

7. An expression construct comprising the nucleic acid sequence according to claim 1.

8. The expression construct of claim 7, wherein the expression construct comprises an autonomously replicating vector or plasmid.

9. The expression construct of claim 7, wherein the expression construct comprises a nucleic acid sequence which integrates into the chromosomal DNA of a host cell.

10. A recombinant host cell which comprises the nucleic acid sequence according to claim 1.

11. A stable culture of a plurality of the cell according to claim 10.

12. The recombinant host cell of claim 10, wherein the expression construct comprises a eukaryotic cell.

13. The recombinant host cell of claim 12, wherein the eukaryotic cell comprises a yeast or filamentous fungal cell.

14. The recombinant host cell of claim 13, wherein the eukaryotic cell comprises a yeast cell of the *Saccharomyces* or *Pichia* genus.

15. The nucleic acid sequence according to claim 1, wherein the variant comprises a sequence which hybridizes under stringent conditions to a nucleic acid consisting of SEQ ID NO:1.

16. The nucleic acid sequence according to claim 1, wherein the variant comprises an analog of SEQ ID NO:1 derived from a species other than *Pichia pastoris* having at least 90% homology to SEQ ID NO:1.

17. A method of producing a protein of interest (POI), comprising
  a) culturing a recombinant host cell line comprising nucleic acid sequence SEQ ID N0:1, or a variant thereof having at least 90% homology to SEQ ID N0:1, operably linked to a heterologous nucleotide sequence encoding a protein of interest (POI), b) cultivating the cell line under conditions to express said POI, and c) recovering the POI.

18. The method according to claim 17, wherein the POI is expressed under growth-limiting conditions.

19. The method according to claim 17, wherein the cell line is cultivated under batch, fed-batch or continuous cultivation conditions, and/or in media containing limited carbon substrate.

20. Method according to claim 17, wherein the POI is a heterologous protein, preferably selected from therapeutic proteins, including antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI.

* * * * *